US005556851A

United States Patent [19]

Maruyama et al.

[11] Patent Number: 5,556,851

[45] Date of Patent: Sep. 17, 1996

[54] CINNOLINE-3-CARBOXYLIC ACID DERIVATIVES

[75] Inventors: Akira Maruyama, Ibaraki-ken; Shigeru Ogawa, Machida; Satoshi Yamazaki, Sagamihara; Akihiro Tobe, Yokohama, all of Japan

[73] Assignee: Mitsubishi Chemical Corporation, Tokyo, Japan

[21] Appl. No.: 286,220

[22] Filed: Aug. 5, 1994

Related U.S. Application Data

[63] Continuation of Ser. No. 29,431, Mar. 10, 1993, Pat. No. 5,391,549.

[30] Foreign Application Priority Data

Mar. 12, 1992 [JP] Japan .................................... 4-53863

[51] Int. Cl.$^6$ .......................... A61K 31/55; A61K 31/50

[52] U.S. Cl. .......................... 514/214; 514/216; 514/248

[58] Field of Search .................................... 514/214, 216, 514/248

[56] References Cited

U.S. PATENT DOCUMENTS

| | | | |
|---|---|---|---|
| 4,910,193 | 3/1990 | Buchheit | 514/216 |
| 4,959,367 | 9/1990 | King | 540/478 |
| 4,985,420 | 1/1991 | Hamminga et al. | 514/211 |
| 4,988,691 | 1/1991 | Benelli et al. | 514/214 |
| 5,106,851 | 4/1992 | Turconi et al. | 514/259 |
| 5,391,549 | 2/1995 | Marvyama | 514/214 |

FOREIGN PATENT DOCUMENTS

| | | |
|---|---|---|
| 0220011 | 4/1987 | European Pat. Off. . |
| 0254584 | 1/1988 | European Pat. Off. . |
| 0255297 | 2/1988 | European Pat. Off. . |
| 0277791 | 8/1988 | European Pat. Off. . |
| 0309423 | 3/1989 | European Pat. Off. . |
| 03061148 | 3/1989 | European Pat. Off. . |
| 0315390 | 5/1989 | European Pat. Off. . |
| 0323077 | 7/1989 | European Pat. Off. . |
| 0337547 | 10/1989 | European Pat. Off. . |
| 0361629 | 4/1990 | European Pat. Off. . |
| 0381422 | 8/1990 | European Pat. Off. . |
| 0458636 | 11/1991 | European Pat. Off. . |
| 0483836 | 5/1992 | European Pat. Off. . |
| 0498721 | 8/1992 | European Pat. Off. . |
| 0504680 | 9/1992 | European Pat. Off. . |
| 0503844 | 9/1992 | European Pat. Off. . |
| 0523013 | 1/1993 | European Pat. Off. . |
| 1-104072 | 4/1989 | Japan . |
| 1-258674 | 10/1989 | Japan . |
| 2125398 | 3/1984 | United Kingdom . |
| 2153821 | 8/1985 | United Kingdom . |
| 2206788 | 1/1989 | United Kingdom . |
| 2231265 | 11/1990 | United Kingdom . |
| 2236751 | 4/1991 | United Kingdom . |
| WO9105783 | 5/1991 | WIPO . |
| WO9117161 | 11/1991 | WIPO . |
| WO92/21658 | 10/1992 | WIPO . |

OTHER PUBLICATIONS

Costall et al, *Reviews in the Neuroscience* 2, pp. 41–65, (1988).

Talley, *Aliment. Pharmacol. Ther.* 6, pp. 273–289 (1992).

Bonate, *Clinical Neuropharmacology*14, pp. 1–16 (1991).

Doria et al., *Chemical Abstract*, vol. 109 No. 231043 (1988).

Evans et al., "Molecular Modeling of 5–$HT_3$ Receptor Ligands", Pharmacology Biochemistry and Behavior, vol. 40, pp. 1033–1040, U.S.A. (1991).

*Primary Examiner*—Emily Bernhardt

*Attorney, Agent, or Firm*—Wenderoth, Lind & Ponack

[57] ABSTRACT

A novel cinnoline derivative having an antagonistic activity against serotonin 5-$HT_3$ receptor, its pharmaceutically acceptable salts, its N-oxide derivatives or solvates thereof, and pharmaceutical formulations containing the same for the prevention and/or treatment of various disorders such as nausea and/or emesis caused by anticancer drugs or X-ray treatment, central nervous disorders such as anxiety and/or neuropathy, gastroenteric diseases such as indigestion, chronic gastritis, digestive ulcer, irritable bowel syndromes and the like, hemicrania, cluster headache, trigeminal neuralgia, arrhythmia and the like.

2 Claims, No Drawings

CINNOLINE-3-CARBOXYLIC ACID DERIVATIVES

This application is a continuation of Ser. No. 08/029,431, filed Mar. 10, 1993, now U.S. Pat. No. 5,391,549.

FIELD OF THE INVENTION

This invention relates to a cinnoline derivative which is pharmaceutically useful as an antagonist against serotonin 5-$HT_3$ receptor, its pharmaceutically acceptable salts, its N-oxide derivatives or solvates thereof, and pharmaceutical compositions containing the same.

BACKGROUND OF THE INVENTION

Metoclopramide has generally been used to treat or control the emesis caused by anticancer agents such as cisplatin though, it does not have sufficient antiemetic activity and, due to its dopamine-like effect, brings other side effects such as extrapyramidal disorders, central nervous actions or the like.

Recently, it was reported that specific antagonists against serotonin 5-$HT_3$ receptor have inhibitory effects on emesis induced by a carcinostatic agent at a small dosage. The Lancet, 1461–1463, 1987.

Examples of compounds known to be antagonistic against 5-$HT_3$ receptor include 8-methyl-8-azabicyclo[3.2.1]octane-3-yl indole-3-carboxylate (ICS 205-930), 1,2,3,9-tetrahydro-9-methyl-3-[(2-methyl-1H-imidazole- 1-yl)methyl] -4H-carbazol-4-on (GR-38032F) and the like. These existing compounds are also accompanied by side effects such as headache, sedation, thirst, diarrhea and the like. The Lancet, 1198, 1987.

Quinolone derivatives such as endo-N-[8-aza-8-methylbicyclo[3.2.1]octane-3-yl]-1-methylquinoline-4-on-3-carboxamide were also reported to be antagonistic against 5-$HT_3$ receptor (GB 2236751A). For the establishment of more acceptable and tolerable treatment of cancer, there is still demand for the development of compounds having anti-emetic activity.

The present inventors became interested in the fact that 5-$HT_3$ receptor antagonists have various pharmacological activities in addition to the anti-emetic activity, for example, a regulating effect on gastroenteric movement, analgetic effect, antianxietic effect and the like. These facts strongly indicate that the development of compounds having antagonistic activity against 5-$HT_3$ receptor can greatly contribute to the improvement of a method and/or prevention of not only the emesis caused by anticancer agents but also various disorders where 5-$HT_3$ receptor antagonists take effect as described above.

Under the circumstances, the present inventors have done research for the purpose of developing novel compounds having an antagonistic activity against 5-$HT_3$ receptor and found that certain cinnoline-3-carboxylic acid derivatives have the desired activity.

Thus, the present invention provides a cinnoline derivative of the following formula (I):

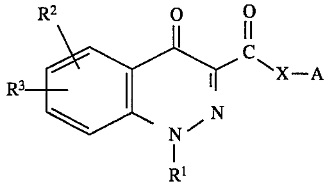

(I)

wherein X is —O— or a group of the formula:

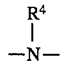

(wherein $R^4$ is a hydrogen atom or $C_1$–$C_5$ alkyl group); A is a group of the formula:

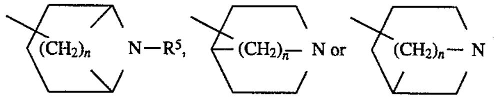

(II) (III) (IV)

(wherein n is an integer selected from 1 to 5; $R^5$ is a hydrogen atom, $C_1$–$C_5$ alkyl group, $C_3$–$C_8$ cycloalkyl group or $C_7$–$C_{15}$ aralkyl group); $R^1$ is a hydrogen atom, $C_1$–$C_5$ alkyl group, $C_2$–$C_5$ alkenyl group, $C_2$–$C_4$ alkynyl group, $C_3$–$C_8$ cycloalkyl group, $C_4$–$C_9$ cycloalkylalkyl group, $C_2$–$C_{10}$ alkoxyalkyl group or $C_7$–$C_{15}$ aralkyl group; and $R^2$ and $R^3$ each is independently a hydrogen atom, halogen atom, trifluoromethyl group, hydroxyl group, $C_1$–$C_5$ alkoxy group, cyano group, nitro group, amino group, $C_1$–$C_5$ alkylamino group, $C_2$–$C_{10}$ dialkylamino group, $C_1$–$C_5$ alkylthio group, $C_1$–$C_5$ alkyl group, $C_3$–$C_8$ cycloalkyl group, $C_7$–$C_{15}$ aralkyl group or $C_2$–$C_{10}$ acyl group or its pharmaceutically acceptable salts, its N-oxide derivatives, or solvates thereof.

More specifically, the present invention provides a cinnoline derivative of the formula (I):

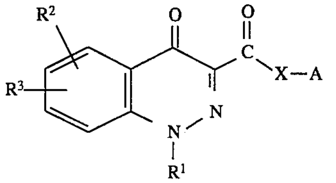

(I)

wherein X is —O— or a group of the formula:

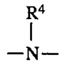

(wherein $R^4$ is a hydrogen atom or $C_1$–$C_5$ alkyl group such as methyl group, propyl group, pentyl group or the like); A is a group of the formula:

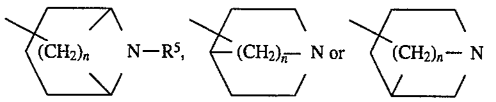

(II) (III) (IV)

(wherein n is an integer selected from 1 to 5, $R^5$ is a hydrogen atom, $C_1$–$C_5$ alkyl group such as methyl group, propyl group, pentyl group or the like, $C_3$–$C_8$ cycloalkyl group such as cyclopropyl group, cyclohexyl group, cyclooctyl group or the like, $C_7$–$C_{15}$ aralkyl group such as benzyl group, phenethyl group or the like); $R^1$ is a hydrogen atom, $C_1$–$C_5$ alkyl group such as methyl group, propyl group, pentyl group or the like, $C_2$–$C_5$ alkenyl group such as vinyl group, pentenyl group or the like, $C_2$–$C_4$ alkynyl group such as ethynyl group, butynyl group or the like, $C_3$–$C_8$ cycloalkyl group such as cyclopropyl group, cyclohexyl group, cyclooctyl group or the like, $C_4$–$C_9$ cycloalkylalkyl group such as cyclopropylmethyl group, cyclopropylbutyl group, cyclohexylmethyl group, cyclohexylbutyl group or the like, $C_2$–$C_{10}$ alkoxyalkyl group such as methoxymethyl group, methoxypentyl group, ethoxybutyl group or the like, or $C_7$–$C_{15}$ aralkyl group such as benzyl group, phenethyl group or the like; $R^2$ and $R^3$ each is independently a hydrogen atom, halogen atom such as fluorine, chlorine, bromine, iodine or the like, trifluoromethyl group, hydroxyl group, $C_1$–$C_5$ alkoxy group such as methoxy group, propoxy group, pentoxy group or the like, cyano group, nitro group, amino group, $C_1$–$C_5$ alkylamino group such as methylamino group, propylamino group, pentylamino group or the like, $C_2$–$C_{10}$ dialkylamino group such as dimethylamino group, dipropylamino group, dipentylamino group or the like, $C_1$–$C_5$ alkylthio group such as methylthio group, propylthio group, pentylthio group or the like, $C_1$–$C_5$ alkyl group such as methyl group, propyl group, pentyl group or the like, $C_3$–$C_8$ cycloalkyl group such as cyclopropyl group, cyclohexyl group, cyclooctyl group or the like, $C_7$–$C_{15}$ aralkyl group such as benzyl group, phenethyl group or the like, or $C_2$–$C_{10}$ acyl group such as acetyl group, butyryl group, heptanoyl group, decanoyl group or the like, or its pharmaceutically acceptable salts, its N-oxide derivatives, or solvates thereof.

As will be understood from the structure, the compound of the formula (I) can form pharmaceutically acceptable salts, for example, an acid addition salt or a quaternary ammonium salt. Examples of acid addition salts include inorganic acid salts such as hydrochloride, hydrobromide, hydroiodide, sulfate, phosphate and the like; and organic acid salts such as oxalate, maleate, fumarate, lactate, malate, succinate, tartrate, benzoate, methanesulfonate and the like. Examples of quaternary ammonium salts are those formed with a lower alkyl halogenide such as methyl iodide, methyl bromide, ethyl iodide, ethyl bromide or the like; a lower alkyl sulfonate such as methylmethanesulfonate, ethylmethanesulfonate or the like; a lower alkyl aryl sulfonate such as methyl p-toluenesulfonate and the like.

The present invention also provides a N-oxide derivative of the compound (I), which can be produced by the N-oxidation at the substituent "A" of the formula (I).

Compounds of the formula (I), physiologically acceptable salts or N-oxide derivatives thereof can all exist in the form of solvates which are also useful for purposes of the present invention and therefore fall within the scope of the present invention.

Furthermore, compounds (I) wherein $R^1$ is a hydrogen atom can be in the form of tautomers which are equivalent to the corresponding compounds of the formula (I) in terms of physiological activities and shown by the following formula (V).

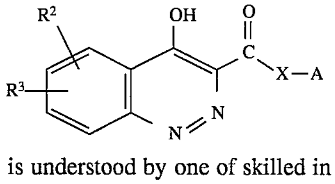
(V)

As is understood by one of skilled in the art, compounds (I) in any possible forms such as stereoisomer, optical isomers, tautomers and the like fall within the scope of the invention as long as the compound has the pharmaceutically useful $5HT_3$ antagonistic activity.

Examples of preferable compounds of the formula (I) are those wherein X is —O— or a group of the formula:

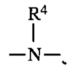

(wherein $R^4$ is a hydrogen atom); A is a group of the formula:

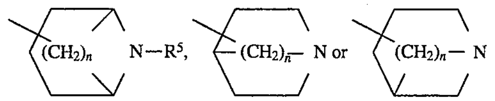
(II) (III) (IV)

(wherein n is an integer selected from 2 to 4, $R^5$ is a $C_1$–$C_5$ alkyl group or $C_7$–$C_{15}$ aralkyl group); $R^1$ is a hydrogen atom, $C_1$–$C_5$ alkyl group, $C_2$–$C_5$ alkenyl group, $C_3$–$C_8$ cycloalkyl group, $C_4$–$C_9$ cycloalkylalkyl group, $C_2$–$C_{10}$ alkoxyalkyl group or $C_7$–$C_{15}$ aralkyl group; $R^2$ and $R^3$ each is independently a hydrogen atom, halogen atom, trifluoromethyl group, hydroxyl group, $C_1$–$C_5$ alkoxy group, cyano group, nitro group, amino group, $C_1$–$C_5$ alkylthio group, $C_1$–$C_5$ alkyl group, $C_7$–$C_{15}$ aralkyl group or $C_2$–$C_{10}$ acyl group.

Examples of more preferable compounds of the formula (I) are those wherein X is —O— or a group of the formula:

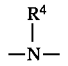

(wherein $R^4$ is a hydrogen atom); A is a group of the formula:

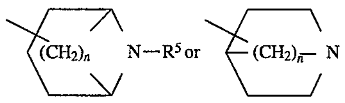
(II) (III)

(wherein n is 2 or 3, $R^5$ is a $C_1$–$C_5$ alkyl group or $C_7$–$C_{15}$ aralkyl group); is a hydrogen atom, $C_1$–$C_5$ alkyl group, $C_2$–$C_5$ alkenyl group or $C_7$–$C_{15}$ aralkyl group; $R^2$ and $R^3$ each is independently a hydrogen atom, halogen atom, $C_1$–$C_5$ alkoxy group or $C_1$–$C_5$ alkyl group.

Examples of the especially preferable compounds of the formula (I) are those wherein X is a group of the formula:

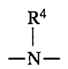

(wherein $R^4$ is a hydrogen atom); A is a group of the formula:

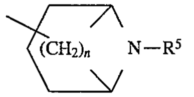
(II)

(wherein n is 2 or 3, $R^5$ is a $C_1$–$C_5$ alkyl group); $R^5$ is a $C_1$–$C_5$ alkyl group; $R^2$ and $R^3$ each is independently a hydrogen atom or halogen atom.

Typical compounds (I) of the present invention are shown in the following Tables 1 to 3. The present invention, however, is not limited to the compounds illustrated in these Tables, but include any compounds (I) and derivatives thereof, as long as the compounds fall within the scope of the invention as herein claimed. In the following Table 1, the term "configuration" represents the type of the bond through which "A" is bound to "X". Thus, the terms "endo" and "exo" represent that A is axial and equatorial, respectively. In the Tables, the term "position" represents the "position of substitutent of A".

TABLE 1

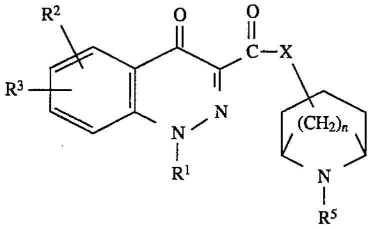

| Compd. No. | $R^1$ | $R^2$ | $R^3$ | X | Config. | position | n | $R^5$ |
|---|---|---|---|---|---|---|---|---|
| 1 | $-H$ | $-H$ | $-H$ | $-O-$ | endo | 3 | 2 | $-CH_3$ |
| 2 | $-H$ | 5-F | $-H$ | $-O-$ | endo | 3 | 2 | $-CH_3$ |
| 3 | $-H$ | 5-Cl | $-H$ | $-O-$ | endo | 3 | 3 | $-CH_3$ |
| 4 | $-H$ | 5-Br | $-H$ | $-O-$ | endo | 3 | 2 | $-CH_3$ |
| 5 | $-H$ | 5-$CH_3$ | $-H$ | $-O-$ | endo | 3 | 2 | $-CH_3$ |
| 6 | $-H$ | 6-$OCH_3$ | $-H$ | $-O-$ | endo | 3 | 2 | $-CH_3$ |
| 7 | $-H$ | 6-OH | $-H$ | $-O-$ | endo | 3 | 2 | $-CH_3$ |
| 8 | $-H$ | 6-$CF_3$ | $-H$ | $-O-$ | endo | 3 | 2 | $-CH_3$ |
| 9 | $-H$ | 6-$COCH_3$ | $-H$ | $-O-$ | endo | 3 | 2 | $-CH_3$ |
| 10 | $-H$ | 7-$SCH_3$ | $-H$ | $-O-$ | endo | 3 | 2 | $-CH_3$ |
| 11 | $-H$ | 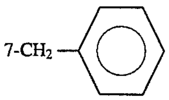 | $-H$ | $-O-$ | endo | 3 | 2 | $-CH_3$ |
| 12 | $-H$ | 7-CN | $-H$ | $-O-$ | endo | 3 | 2 | $-CH_3$ |
| 13 | $-H$ | 8-$NH_2$ | $-H$ | $-O-$ | endo | 3 | 3 | $-CH_3$ |
| 14 | $-H$ | 8-$NO_2$ | $-H$ | $-O-$ | endo | 3 | 2 | 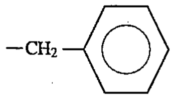 |
| 15 | $-H$ | 5-F | $-H$ | $-O-$ | exo | 3 | 2 | $-CH_3$ |
| 16 | $-CH_3$ | 5-F | 8-F | $-O-$ | endo | 3 | 2 | $-CH_3$ |
| 17 | $-CH_3$ | 5-Cl | 8-$CH_3$ | $-O-$ | endo | 3 | 2 | $-CH_3$ |
| 18 | $-CH_3$ | 5-Cl | $-H$ | $-O-$ | endo | 3 | 2 | $-CH_3$ |
| 19 | $-CH_3$ | 5-F | 8-$CH_3$ | $-O-$ | endo | 3 | 2 | $-CH_3$ |
| 20 | $-CH_3$ | 6-$OCH_3$ | $-H$ | $-O-$ | endo | 3 | 2 | 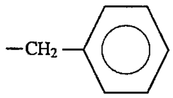 |
| 21 | $-CH_3$ | 6-OH | $-H$ | $-O-$ | endo | 3 | 2 | $-CH_3$ |
| 22 | $-CH_3$ | $-H$ | $-H$ | $-O-$ | endo | 3 | 2 | $-CH_3$ |
| 23 | $-CH_3$ | 8-$CH_3$ | $-H$ | $-O-$ | exo | 3 | 2 | $-CH_3$ |
| 24 | $-C_2H_5$ | $-H$ | $-H$ | $-O-$ | endo | 3 | 2 | $-CH_3$ |
| 25 | $-C_2H_5$ | $-H$ | $-H$ | $-O-$ | exo | 3 | 2 | $-CH_3$ |
| 26 | $-C_2H_5$ | 5-F | $-H$ | $-O-$ | endo | 3 | 2 | $-CH_3$ |
| 27 | $-C_2H_5$ | 5-Cl | $-H$ | $-O-$ | endo | 3 | 2 | $-CH_3$ |
| 28 | $-C_2H_5$ | 5-F | 8-F | $-O-$ | endo | 3 | 3 | $-CH_3$ |
| 29 | $-C_2H_5$ | 6-$CF_3$ | $-H$ | $-O-$ | endo | 3 | 2 | $-CH_3$ |
| 30 | $-C_2H_5$ | 7-$CH_3$ | $-H$ | $-O-$ | endo | 3 | 2 | $-CH_3$ |
| 31 | $-C_2H_5$ | 8-F | $-H$ | $-O-$ | endo | 3 | 2 | $-CH_3$ |
| 32 | n-$C_3H_7$ | $-H$ | $-H$ | $-O-$ | endo | 3 | 2 | $-CH_3$ |
| 33 | n-$C_3H_7$ | $-H$ | $-H$ | $-O-$ | exo | 3 | 2 | $-CH_3$ |
| 34 | n-$C_3H_7$ | 5-F | $-H$ | $-O-$ | endo | 3 | 2 | $-CH_3$ |
| 35 | n-$C_3H_7$ | 6-F | $-H$ | $-O-$ | endo | 3 | 2 | $-CH_3$ |
| 36 | n-$C_3H_7$ | 7-F | $-H$ | $-O-$ | endo | 3 | 2 | $-CH_3$ |
| 37 | n-$C_3H_7$ | 8-F | $-H$ | $-O-$ | endo | 3 | 2 | $-CH_3$ |
| 38 | n-$C_3H_7$ | 5-Cl | $-H$ | $-O-$ | endo | 3 | 2 | 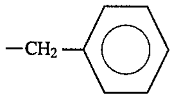 |

TABLE 1-continued

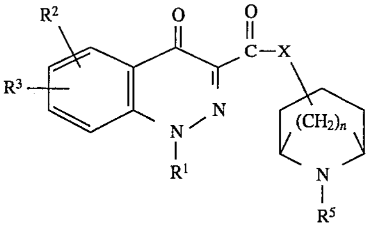

| Compd. No. | $R^1$ | $R^2$ | $R^3$ | X | Config. | position | n | $R^5$ |
|---|---|---|---|---|---|---|---|---|
| 39 | n-$C_3H_7$ | 5-Cl | $-H$ | $-O-$ | endo | 3 | 2 | $-CH_3$ |
| 40 | n-$C_3H_7$ | 5-F | 8-$CH_3$ | $-O-$ | endo | 3 | 2 | $-CH_3$ |
| 41 | n-$C_3H_7$ | 6-CN | $-H$ | $-O-$ | endo | 3 | 2 | $-CH_3$ |
| 42 | n-$C_3H_7$ | 7-$OCH_3$ | $-H$ | $-O-$ | endo | 3 | 2 | $-CH_3$ |
| 43 | n-$C_3H_7$ | 8-$C_2H_5$ | $-H$ | $-O-$ | endo | 3 | 2 | $-CH_3$ |
| 44 | n-$C_3H_7$ | 8-$CH_3$ | $-H$ | $-O-$ | endo | 3 | 2 | $-CH_3$ |
| 45 | n-$C_3H_7$ | 5-$SCH_3$ | $-H$ | $-O-$ | endo | 3 | 2 | $-CH_3$ |
| 46 | n-$C_3H_7$ | 5-F | $-H$ | $-O-$ | endo | 3 | 3 | $-CH_3$ |
| 47 | n-$C_4H_9$ | 5-F | $-H$ | $-O-$ | endo | 3 | 2 | $-CH_3$ |
| 48 | n-$C_4H_9$ | $-H$ | $-H$ | $-O-$ | endo | 3 | 2 | $-CH_3$ |
| 49 | n-$C_4H_9$ | 5-Cl | $-H$ | $-O-$ | endo | 3 | 2 | $-CH_3$ |
| 50 | n-$C_4H_9$ | 5-F | 8-F | $-O-$ | endo | 3 | 2 | $-CH_3$ |
| 51 | 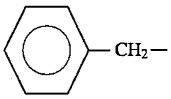 | $-H$ | $-H$ | $-O-$ | endo | 3 | 2 | $-CH_3$ |
| 52 | 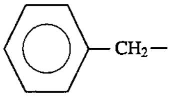 | 5-Cl | $-H$ | $-O-$ | endo | 3 | 2 | $-CH_3$ |
| 53 | $CH_2=CH-CH_2-$ | $-H$ | $-H$ | $-O-$ | endo | 3 | 2 | $-CH_3$ |
| 54 | $CH_2=CH-CH_2-$ | 5-F | $-H$ | $-O-$ | endo | 3 | 2 | $-CH_3$ |
| 55 | 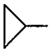 | 5-F | $-H$ | $-O-$ | endo | 3 | 2 | $-CH_3$ |
| 56 | 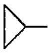 | $-H$ | $-H$ | $-O-$ | endo | 3 | 2 | $-CH_3$ |
| 57 | 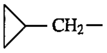 | $-H$ | $-H$ | $-O-$ | endo | 3 | 2 | $-CH_3$ |
| 58 | 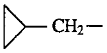 | 5-F | $-H$ | $-O-$ | endo | 3 | 2 | $-CH_3$ |
| 59 | $CH_3OCH_2CH_2-$ | $-H$ | $-H$ | $-O-$ | endo | 3 | 2 | $-CH_3$ |
| 60 | $-H$ | $-H$ | $-H$ | $-NH-$ | endo | 3 | 2 | $-CH_3$ |
| 61 | $-H$ | $-H$ | $-H$ | $-NH-$ | exo | 3 | 2 | $-CH_3$ |
| 62 | $-H$ | $-H$ | $-H$ | $-NH-$ | endo | 3 | 2 | $-CH_3$ |
| 63 | $-H$ | 5-F | $-H$ | $-NH-$ | endo | 3 | 2 | $-CH_3$ |
| 64 | $-H$ | 6-Cl | $-H$ | $-NH-$ | endo | 3 | 2 | $-CH_3$ |
| 65 | $-H$ | 7-CN | $-H$ | $-NH-$ | endo | 3 | 2 | $-CH_3$ |
| 66 | $-H$ | 8-$CH_3$ | $-H$ | $-NH-$ | endo | 3 | 2 | $-CH_3$ |
| 67 | $-H$ | 5-F | 8-$CH_3$ | $-NH-$ | endo | 3 | 2 | $-CH_3$ |
| 68 | $-CH_3$ | $-H$ | $-H$ | $-NH-$ | endo | 3 | 2 | $-CH_3$ |
| 69 | $-CH_3$ | 5-F | 8-F | $-NH-$ | endo | 3 | 2 | $-CH_3$ |
| 70 | $-CH_3$ | 5-CN | $-H$ | $-NH-$ | endo | 3 | 2 | $-CH_3$ |
| 71 | $-CH_3$ | 5-$OCH_3$ | $-H$ | $-NH-$ | endo | 3 | 2 | $-CH_3$ |
| 72 | $-CH_3$ | 5-F | $-H$ | $-NH-$ | endo | 3 | 2 | $-CH_3$ |
| 73 | $-CH_3$ | 6-$C_2H_5$ | $-H$ | $-NH-$ | endo | 3 | 2 | $-CH_3$ |
| 74 | $-CH_3$ | 7-CN | $-H$ | $-NH-$ | endo | 3 | 2 | $-CH_3$ |
| 75 | $-CH_3$ | 8-$NO_2$ | $-H$ | $-NH-$ | endo | 3 | 2 | $-CH_3$ |
| 76 | $-C_2H_5$ | $-H$ | $-H$ | $-NH-$ | endo | 3 | 2 | $-CH_3$ |
| 77 | $-C_2H_5$ | $-H$ | $-H$ | $-NH-$ | exo | 3 | 2 | $-CH_3$ |
| 78 | $-C_2H_5$ | 5-F | $-H$ | $-NH-$ | endo | 3 | 2 | $-CH_3$ |
| 79 | $-C_2H_5$ | 5-Cl | 8-Cl | $-NH-$ | endo | 3 | 2 | $-CH_3$ |
| 80 | $-C_2H_5$ | 6-F | $-H$ | $-NH-$ | endo | 3 | 2 | $-CH_3$ |
| 81 | $-C_2H_5$ | 7-F | $-H$ | $-NH-$ | endo | 3 | 2 | $-CH_3$ |
| 82 | $-C_2H_5$ | 8-F | $-H$ | $-NH-$ | endo | 3 | 2 | $-CH_3$ |
| 83 | $-C_2H_5$ | 5-$CH_3$ | $-H$ | $-NH-$ | endo | 3 | 2 | $-CH_3$ |

TABLE 1-continued

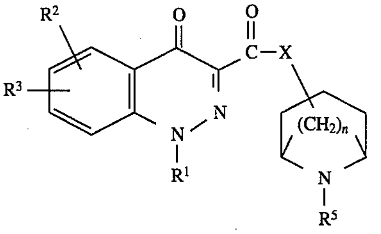

| Compd. No. | $R^1$ | $R^2$ | $R^3$ | X | Config. | position | n | $R^5$ |
|---|---|---|---|---|---|---|---|---|
| 84 | $-C_2H_5$ | 6-$NO_2$ | $-H$ | $-NH-$ | endo | 3 | 2 | $-CH_3$ |
| 85 | $-C_2H_5$ | 7-$SCH_3$ | $-H$ | $-NH-$ | endo | 3 | 2 | $-CH_3$ |
| 86 | n-$C_3H_7$ | $-H$ | $-H$ | $-NH-$ | endo | 3 | 2 | $-CH_3$ |
| 87 | n-$C_3H_7$ | $-H$ | $-H$ | $-NH-$ | exo | 3 | 2 | $-CH_3$ |
| 88 | n-$C_3H_7$ | 5-F | $-H$ | $-NH-$ | endo | 3 | 3 | $-CH_3$ |
| 89 | n-$C_3H_7$ | 5-F | $-H$ | $-NH-$ | endo | 3 | 2 | $-CH_3$ |
| 90 | n-$C_3H_7$ | 5-F | 8-F | $-NH-$ | endo | 3 | 2 | $-CH_3$ |
| 91 | n-$C_3H_7$ | 5-Cl | $-H$ | $-NH-$ | endo | 3 | 2 | $-CH_3$ |
| 92 | n-$C_3H_7$ | 5-Cl | 8-Cl | $-NH-$ | endo | 3 | 2 | $-CH_3$ |
| 93 | n-$C_3H_7$ | 8-Cl | $-H$ | $-NH-$ | endo | 3 | 2 | $-CH_3$ |
| 94 | n-$C_3H_7$ | 5-F | 8-Cl | $-NH-$ | endo | 3 | 2 | $-CH_3$ |
| 95 | n-$C_3H_7$ | 5-F | 8-$CH_3$ | $-NH-$ | endo | 3 | 2 | $-CH_3$ |
| 96 | n-$C_3H_7$ | 5-$NO_2$ | $-H$ | $-NH-$ | endo | 3 | 2 | $-CH_3$ |
| 97 | n-$C_3H_7$ | 5-$OCH_3$ | $-H$ | $-NH-$ | endo | 3 | 2 | $-CH_3$ |
| 98 | n-$C_3H_7$ | 7-$OCH_3$ | $-H$ | $-NH-$ | endo | 3 | 2 | $-CH_3$ |
| 99 | n-$C_3H_7$ | 6-Cl | $-H$ | $-NH-$ | endo | 3 | 2 | $-CH_3$ |
| 100 | n-$C_3H_7$ | 6-F | $-H$ | $-NH-$ | endo | 3 | 2 | $-CH_3$ |
| 101 | n-$C_3H_7$ | 7-F | $-H$ | $-NH-$ | endo | 3 | 2 | $-CH_3$ |
| 102 | n-$C_3H_7$ | 8-F | $-H$ | $-NH-$ | endo | 3 | 2 | $-CH_3$ |
| 103 | n-$C_3H_7$ | 5-$CH_3$ | $-H$ | $-NH-$ | endo | 3 | 2 | $-CH_3$ |
| 104 | n-$C_3H_7$ | 5-F | $-H$ | $-NH-$ | endo | 3 | 3 | $-CH_3$ |
| 105 | n-$C_3H_7$ | 5-F | $-H$ | $-NH-$ | exo | 3 | 2 | $-CH_3$ |
| 106 | n-$C_3H_7$ | 5-F | $-H$ | $-NH-$ | endo | 3 | 2 | $-CH_2-$ 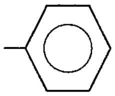 |
| 107 | n-$C_3H_7$ | 5-F | $-H$ | $-NH-$ | endo | 3 | 2 | $-C_2H_5$ |
| 108 | n-$C_3H_7$ | 8-$SCH_3$ | $-H$ | $-NH-$ | endo | 3 | 2 | $-CH_3$ |
| 109 | n-$C_3H_7$ | 7-$CH_3$ | $-H$ | $-NH-$ | endo | 3 | 2 | $-CH_3$ |
| 110 | n-$C_3H_7$ | 8-$NO_2$ | $-H$ | $-NH-$ | endo | 3 | 2 | $-CH_3$ |
| 111 | n-$C_3H_7$ | 8-OH | $-H$ | $-NH-$ | endo | 3 | 2 | $-CH_3$ |
| 112 | n-$C_3H_7$ | 8-$CH_2-$ 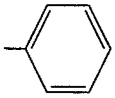 | $-H$ | $-NH-$ | endo | 3 | 2 | $-CH_3$ |
| 113 | n-$C_3H_7$ | 8-$CH_3$ | $-H$ | $-NH-$ | endo | 3 | 2 | $-CH_3$ |
| 114 | n-$C_4H_9$ | $-H$ | $-H$ | $-NH-$ | endo | 3 | 2 | $-CH_3$ |
| 115 | n-$C_4H_9$ | 5-F | $-H$ | $-NH-$ | endo | 3 | 2 | $-CH_3$ |
| 116 | n-$C_4H_9$ | 5-F | $-H$ | $-NH-$ | endo | 3 | 3 | $-CH_3$ |
| 117 | n-$C_4H_9$ | 5-F | 8-F | $-NH-$ | endo | 3 | 2 | $-CH_3$ |
| 118 | n-$C_4H_9$ | 5-F | 8-$CH_3$ | $-NH-$ | endo | 3 | 2 | $-CH_3$ |
| 119 | n-$C_4H_9$ | 5-Cl | $-H$ | $-NH-$ | endo | 3 | 2 | $-CH_3$ |
| 120 | n-$C_4H_9$ | 8-Cl | $-H$ | $-NH-$ | endo | 3 | 2 | $-CH_3$ |
| 121 | n-$C_4H_9$ | 8-F | $-H$ | $-NH-$ | endo | 3 | 2 | $-CH_3$ |
| 122 | n-$C_4H_9$ | 5-F | $-H$ | $-NH-$ | endo | 3 | 2 | $-C_2H_5$ |
| 123 | n-$C_4H_9$ | 5-$NO_2$ | $-H$ | $-NH-$ | endo | 3 | 2 | $-CH_3$ |
| 124 | n-$C_4H_9$ | 6-$SCH_3$ | $-H$ | $-NH-$ | endo | 3 | 2 | $-CH_3$ |
| 125 | n-$C_4H_9$ | 7-$COCH_3$ | $-H$ | $-NH-$ | endo | 3 | 2 | $-CH_3$ |
| 126 | n-$C_4H_9$ | 8-$CH_2-$ 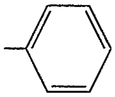 | $-H$ | $-NH-$ | endo | 3 | 2 | $-CH_2-$ 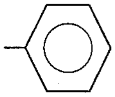 |
| 127 | 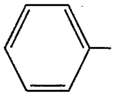 $CH_2-$ | $-H$ | $-H$ | $-NH-$ | endo | 3 | 2 | $-CH_3$ |

TABLE 1-continued

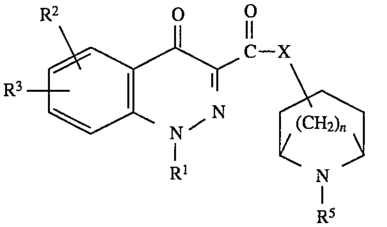

| Compd. No. | $R^1$ | $R^2$ | $R^3$ | X | Config. | position | n | $R^5$ |
|---|---|---|---|---|---|---|---|---|
| 128 | 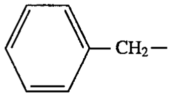 | 5-F | $-H$ | $-NH-$ | endo | 3 | 2 | $-CH_3$ |
| 129 | 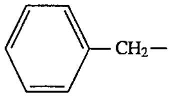 | 5-F | 8-F | $-NH-$ | endo | 3 | 2 | $-CH_3$ |
| 130 | 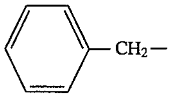 | 5-Cl | $-H$ | $-NH-$ | endo | 3 | 2 | $-CH_3$ |
| 131 | 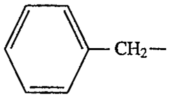 | 5-F | 8-$CH_3$ | $-NH-$ | endo | 3 | 2 | $-CH_3$ |
| 132 | $CH_2=CH-CH_2-$ | $-H$ | $-H$ | $-NH-$ | endo | 3 | 2 | $-CH_3$ |
| 133 | $CH_2=CH-CH_2-$ | 5-F | $-H$ | $-NH-$ | endo | 3 | 2 | $-CH_3$ |
| 134 | $CH_2=CH-CH_2-$ | 5-F | 8-F | $-NH-$ | endo | 3 | 2 | $-CH_3$ |
| 135 | $CH_2=CH-CH_2-$ | 5-Cl | $-H$ | $-NH-$ | endo | 3 | 2 | $-CH_3$ |
| 136 | $CH_2=CH-CH_2-$ | 5-F | $-H$ | $-NH-$ | endo | 3 | 3 | $-CH_3$ |
| 137 | 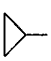 | $-H$ | $-H$ | $-NH-$ | endo | 3 | 2 | $-CH_3$ |
| 138 | 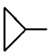 | 5-F | $-H$ | $-NH-$ | endo | 3 | 2 | $-CH_3$ |
| 139 | 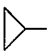 | 5-F | 8-F | $-NH-$ | endo | 3 | 2 | $-CH_3$ |
| 140 | 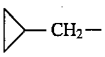 | $-H$ | $-H$ | $-NH-$ | endo | 3 | 2 | $-CH_3$ |
| 141 | 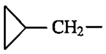 | 5-F | $-H$ | $-NH-$ | endo | 3 | 2 | $-CH_3$ |
| 142 | i-$C_3H_7$ | $-H$ | $-H$ | $-NH-$ | endo | 3 | 2 | $-CH_3$ |
| 143 | i-$C_3H_7$ | 5-F | $-H$ | $-NH-$ | endo | 3 | 2 | $-CH_3$ |
| 144 | i-$C_3H_7$ | 5-F | $-H$ | $-NH-$ | endo | 3 | 3 | $-CH_3$ |
| 145 | i-$C_3H_7$ | 5-F | 5-F | $-NH-$ | endo | 3 | 2 | $-CH_3$ |
| 146 | i-$C_3H_7$ | 5-F | 8-$CH_3$ | $-NH-$ | endo | 3 | 2 | $-CH_3$ |
| 147 | i-$C_4H_9$ | $-H$ | $-H$ | $-NH-$ | endo | 3 | 2 | $-CH_3$ |
| 148 | i-$C_4H_9$ | 5-F | $-H$ | $-NH-$ | endo | 3 | 2 | $-CH_3$ |
| 149 | i-$C_4H_9$ | 5-F | 8-F | $-NH-$ | endo | 3 | 2 | $-CH_3$ |
| 150 | $CH_3OCH_2CH_2-$ | $-H$ | $-H$ | $-NH-$ | endo | 3 | 2 | $-CH_3$ |
| 151 | $CH_3OCH_2CH_2-$ | 5-F | $-H$ | $-NH-$ | endo | 3 | 2 | $-CH_3$ |

TABLE 2

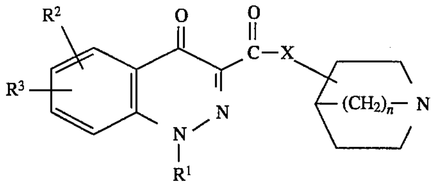

| Compd. No. | $R^1$ | $R^2$ | $R^3$ | X | position | n |
|---|---|---|---|---|---|---|
| 152 | $-H$ | 5-F | $-H$ | $-O-$ | 3 | 2 |
| 153 | $-CH_3$ | 5-F | $-H$ | $-O-$ | 3 | 2 |
| 154 | $-C_2H_5$ | 5-F | $-H$ | $-O-$ | 3 | 2 |
| 155 | n-$C_3H_7$ | $-H$ | $-H$ | $-O-$ | 3 | 2 |
| 156 | n-$C_3H_7$ | 5-F | $-H$ | $-O-$ | 3 | 2 |
| 157 | n-$C_3H_7$ | 5-Cl | $-H$ | $-O-$ | 3 | 2 |
| 158 | n-$C_4H_9$ | $-H$ | $-H$ | $-O-$ | 3 | 2 |
| 159 | n-$C_4H_9$ | 5-F | $-H$ | $-O-$ | 3 | 2 |
| 160 | n-$C_4H_9$ | 5-F | 8-F | $-NH-$ | 3 | 2 |
| 161 | $-H$ | $-H$ | $-H$ | $-NH-$ | 3 | 2 |
| 162 | $-H$ | 5-F | $-H$ | $-NH-$ | 3 | 2 |
| 163 | $-H$ | 5-F | 8-F | $-NH-$ | 3 | 2 |
| 164 | $-CH_3$ | $-H$ | $-H$ | $-NH-$ | 3 | 2 |
| 165 | $-CH_3$ | 5-F | $-H$ | $-NH-$ | 3 | 2 |
| 166 | $-CH_3$ | 5-F | 8-F | $-NH-$ | 3 | 2 |
| 167 | $-C_2H_5$ | $-H$ | $-H$ | $-NH-$ | 3 | 2 |
| 168 | $-C_2H_5$ | 5-F | $-H$ | $-NH-$ | 3 | 2 |
| 169 | $-C_2H_5$ | 5-Cl | $-H$ | $-NH-$ | 3 | 2 |
| 170 | n-$C_3H_7$ | $-H$ | $-H$ | $-NH-$ | 3 | 2 |
| 171 | n-$C_3H_7$ | 5-F | $-H$ | $-NH-$ | 3 | 2 |
| 172 | n-$C_3H_7$ | 5-Cl | $-H$ | $-NH-$ | 3 | 2 |
| 173 | n-$C_3H_7$ | 5-F | 8-F | $-NH-$ | 3 | 2 |
| 174 | n-$C_3H_7$ | 5-F | 8-$CH_3$ | $-NH-$ | 3 | 2 |
| 175 | n-$C_4H_9$ | $-H$ | $-H$ | $-NH-$ | 3 | 2 |
| 176 | n-$C_4H_9$ | 5-F | $-H$ | $-NH-$ | 3 | 2 |
| 177 | n-$C_4H_9$ | 5-F | 8-F | $-NH-$ | 3 | 2 |
| 178 | i-$C_3H_7$ | 5-F | $-H$ | $-NH-$ | 3 | 2 |
| 179 | i-$C_4H_9$ | 5-F | $-H$ | $-NH-$ | 3 | 2 |
| 180 | 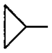 | 5-F | $-H$ | $-NH-$ | 3 | 2 |
| 181 | $-CH_2-$ 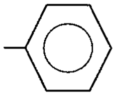 | $-H$ | $-H$ | $-NH-$ | 3 | 2 |

TABLE 3

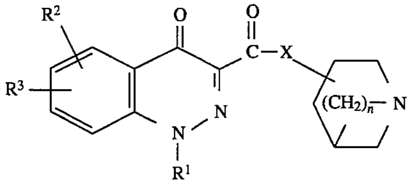

| Compd. No. | $F^1$ | $R^2$ | $R^3$ | X | position | n |
|---|---|---|---|---|---|---|
| 182 | $-H$ | $-H$ | $-H$ | $-O-$ | 4 | 3 |
| 183 | $-CH_3$ | 5-Cl | $-H$ | $-O-$ | 4 | 3 |
| 184 | $-C_2H_5$ | 5-F | 8-F | $-O-$ | 4 | 3 |
| 185 | n-$C_3H_7$ | 5-F | $-H$ | $-O-$ | 4 | 3 |
| 186 | n-$C_4H_9$ | 5-F | 8-$CH_3$ | $-O-$ | 4 | 3 |
| 187 | i-$C_3H_7$ | 5-F | $-H$ | $-O-$ | 4 | 3 |
| 188 | $-H$ | $-H$ | $-H$ | $-NH-$ | 4 | 3 |
| 189 | $-H$ | 5-F | $-H$ | $-NH-$ | 4 | 3 |
| 190 | $-H$ | 5-Cl | $-H$ | $-NH-$ | 4 | 3 |
| 191 | $-H$ | 8-F | $-H$ | $-NH-$ | 4 | 3 |
| 192 | $-CH_3$ | $-H$ | $-H$ | $-NH-$ | 4 | 3 |
| 193 | $-CH_3$ | 5-F | $-H$ | $-NH-$ | 4 | 3 |

TABLE 3-continued

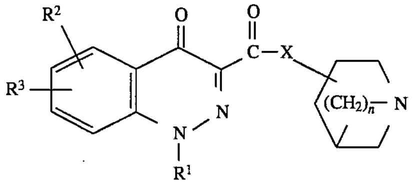

| Compd. No. | $F^1$ | $R^2$ | $R^3$ | X | position | n |
|---|---|---|---|---|---|---|
| 194 | $-CH_3$ | 5-F | 8-F | $-NH-$ | 4 | 3 |
| 195 | $-C_2H_5$ | $-H$ | $-H$ | $-NH-$ | 4 | 3 |
| 196 | $-C_2H_5$ | 5-F | $-H$ | $-NH-$ | 4 | 3 |
| 197 | $-C_2H_5$ | 5-Cl | $-H$ | $-NH-$ | 4 | 3 |
| 198 | $-C_2H_5$ | 5-F | 8-F | $-NH-$ | 4 | 3 |
| 199 | n-$C_3H_7$ | $-H$ | $-H$ | $-NH-$ | 4 | 3 |
| 200 | n-$C_3H_7$ | 5-F | $-H$ | $-NH-$ | 4 | 3 |
| 201 | n-$C_3H_7$ | 5-Cl | $-H$ | $-NH-$ | 4 | 3 |
| 202 | n-$C_3H_7$ | 5-F | 8-F | $-NH-$ | 4 | 3 |
| 203 | n-$C_3H_7$ | 5-$NO_2$ | $-H$ | $-NH-$ | 4 | 3 |
| 204 | n-$C_3H_7$ | 8-F | $-H$ | $-NH-$ | 4 | 3 |
| 205 | n-$C_3H_7$ | 6-F | $-H$ | $-NH-$ | 4 | 3 |

TABLE 3-continued

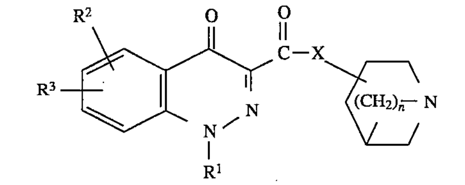

| Compd. No. | $F^1$ | $R^2$ | $R^3$ | X | position | n |
|---|---|---|---|---|---|---|
| 206 | n-$C_3H_7$ | 7-F | —H | —NH— | 4 | 3 |
| 207 | n-$C_4H_9$ | —H | —H | —NH— | 4 | 3 |
| 208 | n-$C_4H_9$ | 5-F | —H | —NH— | 4 | 3 |
| 209 | n-$C_4H_9$ | 6-F | —H | —NH— | 4 | 3 |
| 210 | n-$C_4H_9$ | 7-F | —H | —NH— | 4 | 3 |

The compound (I) of the present invention can be prepared using any of known methods. However, there are some preferable methods as will be hereinafter explained in detail.

For example, the compounds (I) can be prepared by reacting a compound of the general formula (VI):

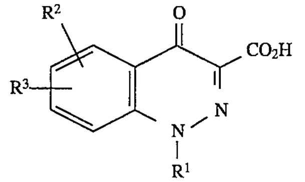

(VI)

wherein $R^1$, $R^2$, and $R^3$ are as defined above in the definition of formula (I), or its reactive derivative obtained by introducing a reactive substituent into the carboxyl group and a compound of the general formula (VII):

H—X—A (VII)

wherein X and A are as defined above in the definition of formula (I) or its precursor (e.g., a compound (VII) in which $R^5$ in the group A is substituted by a benzyl or ethoxycarbonyl group).

Specifically, a compound of the formula (I) wherein X is a group of the formula:

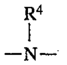

can be prepared by, for instance, the following method (1) or (2).

(1) The carboxyl group of a compound (VI) is reacted with an appropriate reagent such as N,N'-carbonyldiimidazole, dicyclohexylcarbodiimide, N-hydroxysuccinimide, ethyl chloroformate, pentachlorophenol or the like to give a reactive acid derivative, which is then reacted with an amine (VII) wherein X is as defined as just above in a solvent to yield a desired compound (I). Examples of solvents include dichloromethane, chloroform, dichloroethane, toluene, tetrahydrofuran, dioxane, N,N-dimethylformamide, dimethyl sulfoxide and the like. The reaction is generally carried out at a temperature ranging from about 0° to 200° C., preferably about 10° to 120° C. for about 5 min to 25 hr, preferably about 30 min to 10 hr.

(2) A compound (VI) is reacted with an appropriate reagent such as oxalyl chloride, thionyl chloride, phosphorous trichloride, phosphorous pentachloride, phosphorous tribromide or the like to give an acid halide, preferably an acid chloride, which is then reacted with an amine (VII) in a solvent to yield a desired compound (I). Examples of solvents include dichloromethane, dichloroethane, chloroform, toluene, tetrahydrofuran and the like. If necessary, a tertiary amine or a heterocyclic amine such as triethylamine, pyridine or the like may be included in the reaction mixture, or can be used as a solvent. The reaction is generally carried out at a temperature ranging from about −30° to 80° C., preferably about −10° to 50° C. for about 5 min up to 5 hr, preferably about 10 min to 2 hr.

A compound of the formula (I) wherein X is —O— can be prepared by, for instance, the following method (3) or (4).

(3) An alkali metal salt such as lithium, sodium salt or the like of an alcohol (VII) wherein X is as defined just above is obtained by, for example, reacting the alcohol (VII) with n-butyl lithium (hexane solution) in tetrahydrofuran or with sodium hydride in N,N-dimethylformamide. The alkali metal salt of alcohol (VII) is then reacted with a reactive acid derivative (VI) as obtained in the same manner as described in (1) above to yield a desired compound (I). Examples of solvents include tetrahydrofuran, dioxane, N,N-dimethylformamide, dimethyl sulfoxide and the like. The reaction is generally carried out at a temperature ranging from about 0° to 120° C. for about 30 min to 5 hr.

(4) An acid halide, preferably acid chloride of compound (VI) and an alkali metal salt of alcohol (VII), each being prepared in the same manner as in (2) and (3) above, respectively, are reacted in a solvent to yield a desired compound (I). Examples of solvents include tetrahydrofuran, dioxane, chloroform, dimethoxyethane and the like. The reaction is generally carried out at a temperature ranging from about −20° to 60° C. for about 1 min up to 5 hr, preferably about 5 min to 2 hr.

When an endo- or exo-isomer of an amine or alcohol of formula (VII) is used as a starting material, the configuration thereof can be maintained throughout the reactions (1), (2), (3) or (4) to give the final product (I) of the same configuration as that of the starting material (VII). Alternatively, a compound (VII) consisting of exo- and endo-isomers can be reacted according to any of reactions (1) to (4) to give the compound (I) as a mixture of exo- and endo-isomers, which is then resolved by any of conventional methods such as chromatography, crystallization or the like.

A precursor of the compound (VII) such as a protected compound is also used in the reactions (1) to (4). When a precursor is used as a starting material, the reaction product is further subjected to a deprotection procedure such as hydrogenation, ammonia/sodium treatment, alkali hydrolysis or the like.

Although the above-mentioned methods are especially preferable for the production of the desired compound (I), the present invention is by no means restricted to compounds (I) obtained by these methods but is inclusive of all the compounds (I) prepared by any methods known to one skilled in the art.

Thus obtained compounds of the formula (I) can be converted into acid addition salts using a conventional method. Examples of acids usable for the formation of such acid addition salts include inorganic acids such as hydrochloric acid, hydrobromic acid, sulfuric acid, phosphoric acid and the like; organic acids such as acetic acid, oxalic acid, methanesulfonic acid, toluenesulfonic acid, maleic acid, fumaric acid, succinic acid, tartaric acid, lactic acid and the like.

Additionally, the compounds of the formula (I), when heated with an alkyl halide such as methyl iodide, ethyl iodide, methyl bromide or the like in a solvent such as N,N-dimethylformamide, tetrahydrofuran or the like, can give the corresponding quaternary ammonium salts.

An N-oxide derivative of a compound of the formula (I) can be prepared by reacting the compound (I) with an oxidizing agent such as m-chloroperbenzoic acid, peracetic acid, hydrogen peroxide, monopermaleic acid, monoperphthalic acid or the like in a solvent. Examples of solvents include chloroform, methylene chloride, methanol, ethanol, acetic acid, acetone, ethyl ether and the like. The reaction is generally carried out at a temperature ranging from about 0° to 100° C., preferably about 20° to 60° C. for about 10 min to a week.

Alternatively, an alcohol or amine of the formula (VII) can be converted into a N-oxide derivative in the same manner as the above, which is then condensed with a compound (VI) by any of methods (1) to (4) to yield a desired N-oxide of compound (I).

Hydrates or solvates of a compound (I), its pharmaceutically acceptable salt or its N-oxide derivative can be obtained by crystallizing a selected compound from a solvent system consisting of water and a water-soluble solvent such as ethanol.

As will be seen from the results of Experiments below, the compounds (I) of the present invention proved to possess an antagonistic activity against $HT_3$ receptor and are useful in the treatment and/or prevention of emesis caused by anticancer medicines such as cisplatin, nausea and/or emesis due to X-ray treatment, central nervous system disorders such as anxiety and/or mental diseases. They are also useful in the prevention and treatment of various gastroenteric diseases such as indigestion, chronic gastritis, digestive ulcer, irritable colon syndromes or the like, hemicrania, cluster headache, trigeminal neuralgia, arrhythmia or the like.

Thus, the present invention also provides pharmaceutical compositions containing, as an active ingredient, a compound (I) in association with pharmaceutically acceptable carriers therefor.

When the compound of the formula (I), its acid-addition salt, its quaternary ammonium salt, its N-oxide derivative, or a solvate thereof is clinically applied, it can be orally (including sublingual administration) or parenterally administered to humans or animals after 10 formulating into an appropriate form such as tablets, capsules, fine granules, powders, pills, troches, solutions, injectable solutions, suppositories, ointments, plasters or the like in association with a pharmaceutically acceptable carriers therefor.

Tablets and capsules for oral administration are usually formulated in a unit dosage form together with known pharmaceutical additives such as binder, filler, diluent, compressing aid, lubricant, disintegrant, tinction, aromatic, humectant and the like. Tablets can be coated by any of well known methods in the art using an appropriate enteric coating agent.

Examples of fillers suited for the formulations of the present invention include cellulose, mannitol, lactose, or other similar agents. Examples of suitable disintegrants include starch, polyvinylpyrrolidone and starch derivatives such as sodium starch glycolate. Examples of suitable lubricants include magnesium stearate and the like. Examples of pharmaceutically acceptable humectants include sodium lauryl sulfate and the like.

Liquid formulations for oral administration may be in the form of aqueous or oily suspensions, solution, emulsion, syrup, elixir or the like, or a dry product which is reconstructed into a liquid formulation by dissolving into water or an appropriate medium before use. Such liquid formulations include inert additives commonly used in the art, for example, anti-precipitants such as sorbitol, syrup, methyl cellulose, gelatin, hydroxyethyl cellulose, carboxymethyl cellulose, aluminium stearate gel, hydrogenated cooking fat and the like; emulsifiers such as lecithin, sorbitan monooleate, gum arabic and the like; non-aqueous media such as almond oil, purified coconut oil, oily ester (such as glycerin ester), propyleneglycol, ethyl alcohol and the like (cooking oil may be included); preservatives such as methyl p-hydroxybenzoate, ethyl p-hydroxybenzoate, propyl p-hydroxybenzoate, sorbic acid and the like, and conventional aromatics or tinctions, if necessary.

Formulations for oral administration are generally prepared by any of well known methods including mixing, filling, compressing and the like. It is also acceptable to employ the repeat compounding procedures so as to disperse the active ingredient among compositions containing a large amount of fillers.

Formulations for parenteral administration are generally provided as a liquid formulation of unit dosage form, which contains a compound of the invention together with a sterilized medium. Typically, a selected compound of the invention is dissolved or suspended in the medium, depending on the medium and the required concentration of the active ingredient in the formulation. A solution for parenteral administration is generally prepared by dissolving a compound in a medium, filter sterilizing, filling in an appropriate container such as vial or ampoule and sealing. The stability of a product can be improved by freezing a composition containing an active compound and a medium, filling in a vial and removing water under vacuum.

A suspension for parenteral administration is prepared substantially in the same manner as solutions. It is generally conducted by suspending a compound in a medium instead of dissolving, sterilizing by exposing to ethyleneoxide and resuspending in a sterilized media. A surfactant, humectant or the like may also be contained in the suspension so that a compound of the invention may distribute uniformly.

The clinical dose of a compound of the invention should be determined considering various factors such as conditions, weight, age and sex of a patient to be treated. Appropriate daily dosage of the compound of the present invention on oral administration to adult (about 60 kg) is generally about 0.1–500 mg, preferably 0.5–50 mg, which may be administered once or in two to four divisions at appropriate intervals. An appropriate daily dosage for intravenous injection is generally about 0.02–100 mg, preferably 0.1–10 mg, which may be administered once or in two to four divisions at appropriate intervals.

The following Examples further describe the present invention in more detail, but these are illustrative only and are not intended to limit the scope of the invention.

Preparation 1

Ethyl Phenlazocyanoacetate

To a solution of 29.2 g aniline and 79 ml conc. hydrochloric acid in 160 ml water was added dropwise a solution of 22 g sodium nitrite in 55 ml water at 0° C. and stirred for 30 min to yield a solution of diazonium salt. To a solution of 50 ml water and 400 ml ethanol were added 32 g ethyl cyanoacetate and 66 g sodium acetate with stirring, and the diazonium salt solution was added dropwise to the mixture at 0° C. After 2-hour stirring at room temperature, 200 ml water was added to precipitate crystalline materials. Precipitates were separated by filtration, washed with water and dried to yield 69.2 g of the desired compound.

Preparation 2

Ethyl N'-ethyl-phenylhydrazonocyanoacetate

A solution of 50 g ethyl phenylazocyanoacetate, 28.6 g potassium carbonate and 27 ml ethyl iodide in 500 ml acetonitrile was heated to reflux for 4 hr and distilled to remove the solvent. The residue, when purified by chromatography on silica gel, gave 50.1 g of the desired compound as an oil.

Preparation 3

3-Cyano-1-ethyl-1,4-dihydro-4-oxocinnoline

To a solution of 50 g sodium hydroxide, 200 ml water and 200 ml ethanol was added 50 g ethyl N'-ethyl-Phenylhydrazonocyanoacetate as prepared in Preparation 2 above and the resultant mixture stirred for 2 hr at room temperature. After the removal of ethanol by evaporation, to the mixture was added conc. hydrochloric acid to precipitate crystalline materials. Precipitated were separated by filtration, washed with water and dried to yield 34 g of free carboxylic acid, which was stirred with 113 ml thionyl chloride and 340 ml toluene at 80° C. for 2 hr. Thionyl chloride and toluene were removed from the reaction mixture by evaporation. The residue was washed with n-hexane and filtered to yield 36.9 g of carboxylic acid chloride. To a solution of 36.9 g of carboxylic acid chloride in 1 litter 1,2-dichloroethane was added 45.9 g aluminium chloride at room temperature with stirring. The reaction mixture was warmed up to 50° C., stirred for 6 hr and allowed to cool. To the mixture was added gradually 1 l water to separate layers. The organic layer was taken, washed with water, dried with magnesium sulfate and distilled to remove the solvent. The residue was washed with ethyl ether filtered to collect precipitates to yield 25.5 g of the desired compound as a crystal. M.p.=216°–218° C.

Preparation 4

1-Ethyl-1,4-dihydro-4-oxocinnoline-3-carboxylic acid

A solution of 25 g 3-cyano-l-ethyl-1,4-dihydro-4-oxocinnoline, 100 g sodium hydroxide, 400 ml ethanol and 100 ml water was stirred at 70° C. for 3 hr. After the removal of ethanol by evaporation, to the mixture was added conc. hydrochloric acid to precipitate crystalline materials. Precipitates were separated by filtration, washed with water, ethyl ether/ethanol and dried to yield 25.6 g of the desired compound. Mp.=206°–208° C. $^1$H-NMR(DMSO-$d_6$, δ ppm) 1.48 (3H,t), 4.76 (2H,q), 7.76 (1H,t), 8.07 (1H,m), 8.19 (1H,d), 8.33 (1H,d)

Example 1

N-(endo-8-methyl-8-azabicyclo[3.2.1]oct-3-yl)-1,4-methyl-1,4-dihydro-4-oxocinnoline-3-carboxamide hydrochloride (Compound No.68 in Table 1)

A solution of 1.85 g 1-methyl-1,4-dihydro- 4-oxocinnoline-3-carboxylic acid and 2.22 g N,N'-carbonyldiimidazole in 10 ml N,N-dimethylformamide was stirred for 1.5 hr at 60° C. To the reaction mixture was added dropwise a solution of 2.5 g endo-8-methyl-8-azabicyclo[3.2.1]octane-3-amine in 6 ml N,N-dimethylformamide and the mixture stirred for 3 hr at 60° C. and distilled to remove the solvent. The residue, when purified by chromatography on silica gel and recrystallized from chloroform/ethyl acetate, gave the titled compound in the free form. It was treated with 1N hydrochloric acid ethanol solution to yield 1.52 g of the desired compound.

M.P.=250°–255° C. (decomp.) $^1$H-NMR(DMSO-$d_6$, δ ppm) 1.98–2.04 (2H,m), 2.30 (4H,bs), 2.44–2.62 (2H,m), 2.69 (3H,s), 3.83 (2H,bs), 4.12–4.26 (1H,m), 4.29 (3H,s), 7.66–7.76 (1H,m), 7.98–8.08 (2H,m), 8.31 (2H,d), 10.40 (1H,d)

Example 2

1-Ethyl-1,4-dihydro-4-oxocinnoline-3-carboxylic acid (endo-8-methyl-8-azabicyclo[3.2.1]oct-3-yl) ester hydrochloride (Compound No.24 in Table 1)

To a solution of 0.39 g endo-8-methyl-8-azabicyclo[3.2.1]octan-3-ol (tropine) in 5 ml N,N-dimethylformamide was added 0,083 g sodium hydride (64% suspension in oil) at room temperature with stirring. The mixture was stirred for another 30 min to give a solution of tropine sodium salt. To a mixture of 0.4 g 1-ethyl- 1,4-dihydro-4-oxocinnoline-3-carboxylic acid and 0.36 g N,N'-carbonyldiimidazole was added 6 ml N,N-dimethylformamide and stirred at 70° C. for 1 hr to give an imidazolide solution. To the imidazolide solution was added dropwise the previously prepared solution of tropine sodium salt at 70° C. and stirred for 2 hr. After the removal of the solvent by distillation, the residue was dissolved in chloroform, washed with water, dried with sodium sulfate and distilled to remove solvent. The residue, when purified by chromatographies on silica gel and alumina, gave the titled compound in the free form. It was treated with 1N hydrochloric acid ethanol solution to yield 0.06 g of the desired compound. M.P.=269°–276° C. (decomp.) $^1$H-NMR($CDCl_1$, δ ppm) 1.59 (3H,t), 2.14–2.44 (4H, m), 2.70–2.98 (5H,m), 3.02–3.34 (2H,m), 3.79 (2H,bs), 4.58 (2H,q), 5.42–5.56 (1H, m), 7.50–7.72 (2H,m), 7.80–7.92 (1H,m), 8.43 (1H, d)

Example 3

N-(endo-8-methyl-8-azabicyclo[3.2.1]oct-3-yl)-1-ethyl-1,4-dihydro-4-oxocinnoline-3-carboxamide hydrochloride (Compound No.76 in Table 1)

A solution of 0.5 g 1-ethyl-1,4-dihydro- 4-oxocinnoline-3-carboxylic acid and 0.45 g N, N'-carbonyldiimidazole in 5 ml N,N-dimethylformamide was stirred for 1 hr at 60° C. to give a solution of imidazolide. To the solution was added 0.42 g endo-8-methyl-8-azabicyclo[3.2.1]octane-3-amine at 60° C. with stirring and the mixture stirred for 1 hr. After the removal of the solvent by distillation, the residue was extracted with chloroform/water. The organic layer was taken, dried with sodium sulfate, treated with active carbon and distilled to remove the solvent. To the residue was added ethanol to precipitate crystalline materials. Precipitates were collected by filtration and dried to give the desired compound in the free form. It was treated with 1N hydrochloric acid ethanol solution to yield 0.62 g of the desired compound. M.p.=283°–290° C. $^1$H-NMR($CDCl_3$, δ ppm) 1.46 (3H,t), 1.94–2.10 (2H,m), 2.31 (4H,bs), 2.52–2.68 (2H,m), 2.69 (3H,s), 3.87 (2H,bs), 4.08–4.22 (1H,m), 4.69 (2H,q), 7.66 (1H,m), 7.98 (1H,m), 8.12 (1H,d), 8.33 (1H,d)

Example 4

N-(endo-8-methyl-8-azabicyclo[3.2.1]oct-3-yl)-1-propyl-1,4-dihydro-4-oxocinnoline-3-carboxamide hydrochloride (Compound No.86 in Table 1)

A solution of 1.46 g 1-propyl-1,4-dihydro- 4-oxocinnoline-3-carboxylic acid and 1.22 g N,N'-carbonyldiimidazole in 15 ml N,N-dimethylformamide was stirred for 1 hr at 60° C. to give an imidazolide solution. To the solution was added 1.1 g endo-8-methyl-8-azabicyclo[3.2.1]octane-3-amine and the mixture stirred for 2 hr at 60° C. After the removal of the solvent by distillation, the residue was purified by chromatography on silica gel to give the titled compound in the free form. It was treated with 1N hydrochloric acid ethanol solution to yield 1.6 g of the desired compound. M.p.=230°–233° C. $^1$H-NMR($CDCl_3$, δ ppm) 1.06 (3H,t), 2.05 (2H,m), 2.12–2.28 (2H,m), 2.28–2.60 (4H,m) 2.82 (3H,s), 2.90–3.20 (2H,m), 3.84 (2H,bs), 4.50 (1H,m), 4.63 (2H,m), 7.56–8.76 (2H,m), 7.87 (1H,m), 8.45 (1H,d), 10.78 (1H,d)

Example 5

N-(1-azabicyclo[2.2.2]oct-3-yl)-l-propyl-1,4-dihydro-4-oxocinnoline-3-carboxamide hydrochloride (Compound No.170 in Table 2)

A solution of 1.5 g 1-propyl-1,4-dihydro- 4-oxocinnoline-3-carboxylic acid and 1.26 g N,N'-carbonyldiimidazole in 15 ml N,N-dimethylformamide was stirred for 1 hr at 60° C. to give an imidazolide solution. To the solution was added 0.98 g 1-azabicyclo[2.2.2]octane-3-amine and the mixture stirred for 2 hr at 60° C. After the removal of the solvent by distillation, the residue was purified by chromatography on silica gel to give the titled compound in the free form. It was treated with 1N hydrochloric acid ethanol solution to yield 1.0 g of the desired compound. M.p.=268°–271° C. $^1$H-NMR($CDCl_3$, δ ppm) 1.06 (3H,t), 1.90–2.16 (5H,m), 2.22–2.40 (1H,m), 2.40–2.50 (1H,m), 3.10–3.50 (5H,m), 3.70–3.90 (1H,m), 4.50–4.70 (3H,m), 7.56–7.76 (2H,m), 7.84–7.96 (1H,m), 8.45 (1H,d)

Example 6

7-Fluoro-N-(endo-8-methyl-8-azabicyclo[3.21]oct-3-yl)-1-propyl-,1,4-dihydro-4-oxocinnoline-3-carboxamide hydrochloride (Compound No.101 in Table 1)

To 15 ml N,N-dimethylformamide was added 1.0 g 7-fluoro-1-propyl-1,4-dihydro-4-oxocinnoline-3-carboxylic acid and 0.71 g N,N'-carbonyldiimidazole at room temperature and stirred for 2 hr to obtain an imidazolide solution. To the solution was added dropwise a solution of 0.62 g endo-8-methyl-8-azabicyclo[3.2.1]octane-3-amine in 2 ml N,N-dimethylformamide and the mixture stirred for 1 hr at room temperature and allowed to stand for overnight. After the removal of the solvent by distillation, the residue was dissolved in chloroform. The solution was washed with water, dried with magnesium sulfate and evaporated to remove the solvent. The resultant crystalline materials were recrystallized from chloroform/ethyl acetate to give the titled compound in the free form. It was treated with 1N hydrochloric acid ethanol solution to yield 0.90 g of the desired compound.

M.p.=294°–298° C. (decomp.). $^1$H-NMR(DMSO-$d_6$, δ ppm) 0.95 (3H,t), 1.80–1.98 (2H,m), 1.98–2.16 (2H,m), 2.31 (4H,bs), 2.42–2.62 (2H,m), 2.64–2.90 (3H,m), 3.89 (1H,bs), 4.04–4.28 (1H,m), 4.40–4.66 (2H,m), 7.50–7.62 (1H,m), 7.98–8.10 (1H,m), 8.32–8.46 (1H,m), 10.20 (1H,d)

Example 7

6-Fluoro-N-(endo-8-methyl-8-azabicyclo[3.2.1]oct-3-yl)-1-propyl-1,4-dihydro-4-oxocinnoline-3-carboxamide hydrochloride (Compound No.100 in Table 1)

To a solution of 1.0 g 6-fluoro-1-propyl-1, 4-dihydro-4-oxocinnoline-3-carboxylic acid in 20 ml N,N-dimethylformamide was added 0.78 g N,N'-carbonyldiimidazole at room temperature and the mixture stirred for 1.5 hr to obtain an imidazolide solution. To the solution was added dropwise a solution of 0.62 g endo-8-methyl-8-azabicyclo[3.2.1]octane-3-amine in 5 ml N,N-dimethylformamide at room temperature and the mixture stirred for another 4 hr. The reaction mixture was evaporated to remove the solvent and the residue was dissolved in chloroform, washed with water and extracted with 3N HCl solution. After washing with chloroform (x2), the acidic aqueous solution was made basic with sodium hydrogen carbonate and extracted with chloroform (x4). The organic layer was taken, dried with sodium sulfate and evaporated to remove the solvent. The residue was recrystallized from chloroform/ethyl acetate to give the titled compound in the free form. It was treated with 1N hydrochloric acid ethanol solution to yield 0.92 g of the desired compound. M.p.=246°–251° C. $^1$H-NMR($CDCl_3$, δ ppm) 1.06 (3H,t), 1.96–2.20 (2H,m), 2.14–2.26 (2H,m), 2.30–2.64 (4H,m), 2.78 (3H,m), 3.10–3.30 (2H,m), 3.81 (2H,bs), 4.44–4.58 (1H,m), 4.58–4.70 (2H,m), 7.56–7.82 (2H,m), 8.04–8.16 (1H,m), 10.60 (1H,d)

Example 8

5-Fluoro-N-(endo-8-methyl-8-azabicyclo[3.2.1]oct-3-yl)-1-propyl-1,4-dihydro-4-oxocinnoline-3-carboxamide hydrochloride (Compound No.89 in Table 1)

To a solution of 2.0 g 5-fluoro-1-propyl- 1,4- dihydro-4-oxocinnoline-3-carboxylic acid in 20 ml N,N-dimethylformamide was added 1.43 g N,N'-carbonyldiimidazole at room temperature and the mixture stirred for 2 hr to obtain an imidazolide solution. To the solution was added dropwise a solution of 1.29 g endo-8-methyl-8-azabicyclo[3.2.1]octane-3-amine in 6 ml N,N-dimethylformamide at room temperature and the mixture stirred for another 5 hr. The reaction mixture was distilled to remove the solvent and the residue dissolved in chloroform. The solution was washed with water, dried with magnesium sulfate and evaporated to remove the solvent. The residue was purified by chromatography on silica gel and recrystallized from ethyl acetate/n-hexane to give the titled compound in the free form. It was treated with 1N hydrochloric acid ethanol solution to yield 1.98 g of the desired compound. M.p.=239°–243° C. $^1$H-NMR(DMSO-d6, δ ppm) 0.95 (3H,t), 1.78–1.98 (2H,m), 1.98–2.16 (2H,m), 2.30 (4H,bs), 2.56–2.62 (2H,m), 2.68 (3H,s), 3.88 (2H,bs), 4.04–4.20 ($^1$H,m), 4.48–4.62 (2H,m), 7.32–7.44 (1H,m), 7.82–7.98 (2H,m), 10.01 ($^1$H,d)

Example 9

8-Fluoro-N-(endo-8-methyl-8-azabicyclo[3.2.1]oct-3-yl)-1-propyl-1,4-dihydro-4-oxocinnoline-3-carboxamide hydrochloride (Compound No.102 in Table 1)

To a solution of 1.0 g 8-fluoro-l-propyl- 1,4-dihydro-4-oxocinnoline-3-carboxylic acid in 10 ml N,N-dimethylformamide was added 0.78 g N,N'-carbonyldiimidazole at room temperature and the mixture stirred for 30 min to obtain a solution of imidazolide. To the solution was added dropwise a solution of 0.62 g endo-8-methyl-8-azabicyclo [3.2.1]octane-3-amine in 2 ml N,N-dimethylformamide at room temperature and the mixture stirred for another 6 hr. The reaction mixture was evaporated to remove the solvent and the residue was dissolved in chloroform and extracted with aqueous 3N HCl solution. The aqueous solution was made basic with sodium hydrogen carbonate and extracted with chloroform. The organic layer was taken, dried with sodium sulfate and evaporated to remove the solvent. The residue was recrystallized from chloroform/ethyl acetate to give the titled compound in the free form. It was treated with 1N hydrochloric acid ethanol solution to yield 1.04 g of the desired compound. M.p.=290°–292° C. (decomp.) $^1$H-NMR($CDCl_3$, δ ppm) 1.02 (3H,t), 1.90–2.10 (2H,m), 2.10–2.26 (2H,m), 2.28–2.66 (4H,m), 2.81 (3H,m), 3.02–3.32 (2H,m), 3.83 (2H,bs), 4.44–4.58 ($^1$H,m), 4.64–4.84 (2H,m), 7.48–7.70 (2H,m), 8.22–8.36 ($^1$H,m), 10.54 (1H,d)

Example 10

5-Fluoro-N-(1-azabicyclo[2.2.2]oct-3-yl)-1-propyl- 1,4-dihydro-4-oxocinnoline-3-carboxamide hydrochloride (Compound No.171 in Table 2)

To a solution of 0.28 g 5-fluoro-l-propyl-1,4-dihydro-4-oxocinnoline-3-carboxylic acid in 4 ml N,N-dimethylformamide was added 0.24 g N,N'-carbonyldiimidazole at room temperature and the mixture stirred for 1 hr. To the solution was added dropwise a solution of 0.17 g 1azabicyclo-[2.2.2] octane-3-amine in 2 ml N,N-dimethylformamide at room temperature and the mixture stirred for 2 hr. The reaction mixture was evaporated to remove the solvent and the residue dissolved in chloroform. The solution was washed with saturated sodium hydrogen carbonate solution, dried with magnesium sulfate and evaporated to remove the solvent. The residue was recrystallized from ethyl acetate/chloroform/n-hexane to give the titled compound in the free form. It was treated with 1N hydrochloric acid ethanol solution to yield 0.33 g of the desired compound. M.p.= 224°–228° C. $^1$H-NMR($CDCl_3$, δ ppm) 1.06 (3H,t), 1.90–2.20 (5H,m), 2.22–2.40 ($^1$H,m), 2.40–2.50 (1H,m), 3.12–3.28 (1H,m), 3.28–3.52 (4H,m), 3.76–3.92 (1H,m), 4.46–4.70 (3H,m), 7.16–7.30 (1H,m), 7.50 (1H,d), 7.80–7.96 (1H,m), 10.46 (1H,d)

Example 11

8-Fluoro-1-propyl-1,4-dihydro-4-oxocinnoline-3-carboxylic acid (endo-8-methyl-8-azabicyclo[3.2.1]oct-3-yl) ester hydrochloride (Compound No.37 in Table 1)

To a solution of 0.31 g endo-8-methyl- 8-azabicyclo [3.2.1]octane-3-ol (tropine) in 4 ml N,N-dimethylformamide was added 0.067 g sodium hydride (60% suspension in oil) at room temperature and the mixture stirred for 1 hr to give a solution of tropine sodium salt. To a solution of 0.38 g 8-fluoro-l-propyl-1,4-dihydro-4-oxocinnoline-3-carboxylic acid in 4 ml N,N-dimethylformamide was added 0.37 g N,N'-carbonyldiimidazole at room temperature and the mixture stirred for 1 hr to give an imidazolide solution. To the solution was added dropwise the solution of tropine sodium salt at room temperature and the mixture stirred for 1 hr. The reaction mixture was evaporated to remove the solvent and the residue was dissolved in chloroform, washed with potassium carbonate solution and extracted with aqueous 3N HCl solution. The aqueous layer was taken, made basic with sodium hydrogen carbonate and extracted with chloroform. The organic layer was taken, dried with magnesium sulfate and evaporated to remove the solvent. The residue, when purified by chromatography on silica gel, gave the titled compound in the free form. It was then treated with 1N hydrochloric acid ethanol solution to yield 0.28 g of the desired compound. M.P.=244°–247° C. $^1$H-NMR($CDCl_3$, δ ppm) 1.02 (3H,t), 1.86–2.08 (2H,m), 2.12–2.36 (4H,m), 2.66–2.94 (5H,m), 3.06–3.28 (2H,m), 3.79 (2H,bs), 4.52–4.70 (2H,m), 5.40–5.56 (1H,m), 7.40–7.62 (2H,m), 8.16–8.32 (1H,m)

Example 12

5-Fluoro-l-propyl-1,4-dihydro-4-oxocinnoline-3-carboxylic acid (endo-8-methyl-8-azabicyclo[3.2.1]oct-3-yl) ester hydrochloride (Compound No.34 in Table 1)

To a solution of 2.4 g endo-8-methyl-8-azabicyclo[3.2.1] octane-3-ol (tropine) in 20 ml tetrahydrofuran was added dropwise 9.1 ml 15% n-butyllithium-n-hexane solution at 0° C. and the mixture stirred for 1 hr at room temperature to give a solution of tropine lithium salt. To a solution of 3.3 g 5-fluoro-1-propyl- 1,4-dihydro-4-oxocinnoline-3-carboxylic acid in 35 ml N,N-dimethylformamide was added 2.78 g N,N'-carbonyldiimidazole at room temperature and the mixture stirred for 1 hr to give an imidazolide solution. To the solution was added dropwise the solution of tropine lithium salt at room temperature and the mixture stirred for 2 hr. The reaction mixture was evaporated to remove the solvent and the residue was dissolved in chloroform, washed with 5% potassium carbonate solution, dried with magnesium sulfate and evaporated to remove the solvent. The residue was purified by chromatography on silica gel and recrystallized from ethyl acetate/n-hexane to give the titled compound in the free form. It was then treated with 1N hydrochloric acid ethanol solution to yield 1.6 g of the desired compound. M.P.=230°–237° C. $^1$H-NMR(DMSO-d6, δ ppm) 0.93 (1H,t), 1.78–1.96 (2H,m), 1.98–2.16 (2H, m), 2.12–2.30 (2H,m), 2.36–2.48 (2H,m), 2.59 (1H,m), 2.69 (3H,s), 3.85 (2H,bs), 4.45 (2H,t), 5.16–5.24 (1H,m), 7.26–7.40 (1H,m), 7.79 (1H,d), 7.86–7.98 (1H,m)

Example 13

5-Fluoro-N-(endo-8-methyl-8-azabicyclo[3.2.1]oct-3-yl)-1-ethyl-1,4-dihydro-4-oxocinnoline-3-carboxamide hydrochloride (Compound No.78 in Table 1)

To a solution of 0.6 g 5-fluoro-l-ethyl- 1,4-dihydro-4-oxocinnoline-3-carboxylic acid in 6 ml N,N-dimethylformamide was added 0.44 g N,N'-carbonyldiimidazole at room temperature and the mixture stirred for 1 hr to obtain an imidazolide solution. To the solution was added 0.27 g endo-8-methyl-8-azabicyclo[3.2.1]octane-3-amine at room temperature, stirred for 3 hour and allowed to stand for overnight. The reaction mixture was evaporated to remove the solvent and the residue dissolved in chloroform. The solution was washed with aqueous potassium carbonate solution, dried with magnesium sulfate and evaporated to remove the solvent. To the residue was added ethyl ether and the precipitates were collected by filtration to obtain the titled compound in the free form. It was treated with 1N hydrochloric acid ethanol solution to yield 0.61 g of the desired compound. M.p.=178°–184° C. $^1$H-NMR(DMSO-$d_6$, δ ppm) 1.43 (3H,t), 1.96–2.14 (2H,m), 2.30 (4H,bs), 2.48–2.76 (5H,m), 3.87 (2H,bs), 4.02–4.18 (1H,m), 4.62 (2H,q), 7.24–7.46 (1H,m), 7.79 (1H,d), 7.88–8.02 (1H,m), 10.04 (1H,d)

Example 14

N-(endo-8-methyl-8-azabicyclo[3.2.1]oct-3-yl)-1-( 2-propenyl]1,4-dihydro-4-oxocinnoline-3-carboxamide 1/2 L-tartrate (Compound No.132 in Table 1)

A solution of 0.6 g 1-(2-propenyl)-l,4-dihydro- 4-oxocinnoline-3-carboxylic acid and 0.55 g N,N'-carbonyldiimidazole in 6 ml N,N-dimethylformamide was stirred at room temperature for 1 hr and then at 50° C. for 10 min. To the solution was added 0.4 g endo-8-methyl-8-azabicyclo[3.2.1] octane-3-amine and the mixture stirred for 12 hr at room temperature and evaporated to remove the solvent. To the residue was added aqueous potassium carbonate solution and the mixture extracted with chloroform (x2). The organic layer was taken and extracted with aqueous 3N hydrochloric acid solution (x2). The aqueous layer was taken, made basic with potassium carbonate and extracted with chloroform (x2). The extract was dried with magnesium sulfate and evaporated to remove the solvent. The residue was washed with ethyl ether/n-hexane and filtered to obtain the titled compound in the free form. The product was then dissolved in 5 ml methanol and mixed with a solution of 0.15 g L-(+)-tartaric acid in 5 ml methanol at room temperature. When the methanol was removed from the mixture by distillation under vacuum, 0.80 g of the desired compound was obtained as an yellowish solid. M.p. =194°–198° C. $^1$H-NMR($CDCl_3$, δ ppm) 1.98–2.20 (2H,m), 2.26–2.56 (4H, m), 2.62–2.94 (5H,m), 3.68–3.90 (2H,m), 4.36–4.50 (2H, m), 5.18–5.46 (4H,m), 5.98–6.18 (1H,m), 7.52–7.72 (2H, m), 7.78–7.90 (1H,m), 8.40–8.50 (1H,m), 10.67 (1H,d)

Example 15

1-(2-propenyl),-1,4-dihydro-4-oxocinnoline-3-carboxylic acid(endo-8-methyl-8-azabicyclo[3.2.1]oct-3-yl) ester 1/2 L-(+)-tartrate (Compound No.53 in Table 1)

To a solution of 0.55 g endo-8-methyl-8-azabicyclo[3.2.1] octane-3-ol (tropine) in 6 ml N,N-dimethylformamide was added 0.125 g sodium hydride (60% suspension in oil) at room temperature and the mixture stirred for 1 hr to give a solution of tropine sodium salt.

A solution of 0.6 g 1-(2-propenyl)-1,4-dihydro- 4-oxocinnoline-3-carboxylic acid and 0.63 g N,N'-carbonyldiimidazole in 6 ml N,N-dimethylformamide was stirred at room temperature for 1 hr to give an imidazolide solution. To the imidazolide solution was added the solution of tropine sodium salt and the mixture was stirred for another 4 hr at room temperature. After the addition of a slight amount of acetic acid, the mixture was evaporated to remove the solvent. To the residue was added aqueous potassium carbonate solution and the mixture extracted with chloroform. The organic layer was taken and extracted with aqueous 3N HCl solution. The aqueous layer was taken, made basic with potassium carbonate and extracted with chloroform. The organic layer was dried with magnesium sulfate and evaporated. To the residue was added ethyl acetate/ethyl ether to precipitate the titled compound in the free form. The product was dissolved in 5 ml methanol, mixed with 0.029 mg L-(+)-tartaric acid and stirred for 30 min at room temperature. The mixture was evaporated to remove the solvent. The residue was washed with ethyl acetate to give 0.16 g of the desired compound. M.p.=213°–215° C. $^1$H-NMR ( $CDCl_3$, δ ppm ) 2.04–2.32 (4H,m), 2.54–2.90 (7H,m), 3.62–3.78 (2H,m), 4.40 (1H,s), 5.08–5.18 (2H,m), 5.24–5.48 (3H,m), 5.94–6.14 (1H,m), 7.50–7.59 (2H,m), 7.76–7.84 (1H,m), 8.38–8.46 (1H,m)

Examples 16–31

The following compounds were prepared in the similar manner as described in Examples 1 to 15.

(1) 1-Methyl-1,4-dihydro-4-oxocinnoline-3-carboxylic acid (endo-8-methyl-8-azabicyclo[3.2.1]oct-3-yl) ester hydrochloride (Compound No.22 in Table 1)

M.P.=270°–280° C. (decomp.) $^1$H-NMR(DMSO-$d_6$/$D_2O$, δ ppm) 2.22–2.76 (8H,m), 2.85 (3H,s), 3.90–4.10 (2H,m), 4.21 (3H,s), 5.30–5.42 (1H,m), 7.60–7.72 (1H,m), 7.72–7.82 (1H,m), 7.88–8.00 (1H,m), 8.08–8.18 (1H,m)

(2) N-(endo-8-methyl-8-azabicyclo[3.2.1]oct-3-yl)- 4-oxocinnoline-3-carboxamide hydrochloride (Compound No.60 in Table 1)

M.P. >300° C. $^1$H-NMR ( DMSO-$d_6$, δ ppm ) 1.96–2.16 (2H,m), 2.20–2.40 (3H,m), 2.40–2.74 (6H,m), 3.82–3.98 (2H,m), 4.10–4.24 (1H,m), 7.52–7.64 (1H,m), 7.82–7.98 (2H,m), 8.20–8.30 (1H,m), 10.42 (1H,d)

(3) N-( 1-azabicyclo[2.2.2 ]oct-3-yl)-1-benzyl-1, 4-dihydro-oxocinnoline- 3 -carboxamide hydrochloride (Compound No. 181 in Table 2)

M.p.=184°–186° C. $^1$H-NMR($CDCl_3$, δ ppm) 1.90–2.56 (5H,m), 3.14–3.54 (5H,m), 3.70–3.88 (1H,m), 4.54–4.70 (1H,m), 5.89 (2H,s), 7.20–7.42 (5H,m), 7.52–7.68 (2H,m), 7.70–7.82 (1H,m), 8.40–8.50 (1H,m), 10.74 (1H,d)

(4) N-( 1-azabicyclo[2.2.2 ]oct-3-yl)-1-butyl-1,4-dihydro-4-oxocinnoline- 3 -carboxamide hydrochloride (Compound No. 175 in Table 2)

M.p.=149°–150° C. $^1$H-NMR ($CDCl_3$, δ ppm ) 1.00 (3H,t), 1.28–1.70 (3H,m), 1.70–1.84 (2H,m), 1.90–2.10 (3H, m), 2.10–2.18 (1H,m), 2.70–3.14 (4H,m), 3.42–3.58 (1H, m), 4.20–4.30 (1H,m), 4.56–4.74 (2H,t), 7.54–7.76 (2H,m), 7.80–7.94 (1H,m), 8.46 (1H,d), 10.43 (1H,d) (5) 1-Butyl-N-( endo-8-methyl-8-azabicyclo[3.2.1]oct-3-yl)-1,4-dihydro-4-oxocinnoline-3-carboxamide hydrochloride (Compound No. 114 in Table 1 )

M.p. =261°–263° C. $^1$H-NMR($CDCl_3$, δ ppm) 0.96 (3H, t), 1.38–1.56 (2H,m), 1.86–2.08 (2H,m), 2.08–2.68 (5H,m), 2.76 (3H,s), 3.08–3.30 (1H,m), 3.68–3.92 (2H,m), 4.38–4.54 (1H,m), 4.62 (2H,t), 7.52–7.74 (2H,m), 7.80–7.92 (1H,m), 8.38–8.50 (1H,m), 10.64 (1H,d)

(6) N-(endo-8-methyl-8-azabicyclo[3.2.1]oct-3-yl)- 7-methoxy- 1 -propyl - 1,4 -dihydro-4-oxocinnoline - 3-carboxamide hydrochloride (Compound No. 98 in Table 1)

M.p.=268°–273° C. (decomp.) $^1$H-NMR ( DMSO-$d_6$, δ ppm) 0.95 (3H,t), 1.80–1.98 (2H,m), 1.98–2.12 (2H,m), 2.20–2.42 (4H,m), 2.46–2.86 (5H,m), 3.82–3.96 (2H,m), 4.00 (3H,s), 4.08–4.28 (1H,m), 4.59 (2H,t), 7.20–7.34 (2H, m), 8.24 (1H,d), 10.50 (1H,d)

(7) N-(endo-8-methyl-8-azabicyclo[3.2.1]oct-3-yl)- 5-methyl-1-propyl-1,4-dihydro-4-oxocinnoline-3-carboxamide hydrochloride (Compound No.103 in Table 1)

M.p.=204°–206° C. $^1$H-NMR(DMSO-$d_6$, δ ppm) 0.96 (3H,t), 1.86–1.98 (2H,m), 1.98–2.14 (2H,m), 2.20–2.46 (3H, m), 2.50–2.80 (6H,m), 2.84 (3H,s), 3.80–4.00 (2H,m), 4.06–4.22 (1H,m), 4.50–4.62 (2H,m), 7.34 (1H,s), 7.72–7.92 (2H,m), 10.28(1H,d)

(8) N-(endo-8-methyl-8-azabicyclo[3.2.1]oct-3-yl)- 7-methyl-1-propyl-1,4-dihydro-4-oxocinnoline-3-carboxamide hydrochloride (Compound No.109 in Table 1)

M.p.=288°–293° C. (decomp.) $^1$H-NMR(DMSO-$d_6$, δ ppm) 0.96 (3H,t), 1.82–1.98 (2H,m), 1.82–2.16 (2H,m), 2.20–2.42 (4H,m), 2.52–2.64 (4H,m), 2.70 (3H,s), 3.82–3.98 (2H,m), 4.12–4.26 (1H,m), 4.50–4.68 (2H,t), 7.50 (1H,d), 7.92 (1H,s), 8.22 (1H,d), 10.48 (1H,d)

(9) N-(endo-8-methyl-8-azabicyclo[3.2.1]oct-3-yl )- 8-methyl-1-propyl-1,4-dihydro-4-oxocinnoline-3-carboxamide hydrochloride (Compound No. 113 in Table 1)

M.p.=273°–277° C. $^1$H-NMR($CDCl_3$, δ ppm) 0.96 (3H,t), 1.76–1.98 (3H,m), 2.06–2.24 (2H,m), 2.24–2.66 (4H,m), 2.80 (3H,s), 2.86 (3H,s), 3.06–3.28 (1H,m), 3.76–3.92 (2H, m), 4.42–4.58 (1H,m), 4.74–4.90 (2H,m), 7.48 (1H,t), 7.68 (1H,d), 8.36 (1H,d), 10.70 (1H,d)

(10) 8-Methyl-l-propyl-1,4-dihydro-4-oxocinnoline-3-carboxylic acid (endo-8-methyl-8-azabicyclo[3.2.1]oct-3-yl) ester hydrochloride (Compound No. 44 in Table 1)

M.p.=246°–249° C. $^1$H-NMR($CDCl_3$, δ ppm) 0.95 (3H,t), 1.70–1.98 (2H,m), 2.08–2.38 (4H,m), 2.56–2.98 (8H,m), 3.00–3.28 (2H,m), 3.60–3.90 (2H,m), 4.42– 4.76 (2H,m), 5.32–5.58 (1H,m),7.42 (1H,t), 7.62 (1H,d), 8.32 (1H,d)

(11) 5-Chloro-N-(endo-8-methyl-8-azabicyclo[3.2.1]oct-3-yl) -1-propyl-1,4-dihydro-4-oxocinnoline-3-carboxamide hydrochloride (Compound No. 91 in Table 1)

M.p. =270°–278° C. (decomp.) $^1$H-NMR (DMSO-$d_6$ , δ ppm ) 0.96 (3H,t), 1.76–1.96 (2H,m), 1.96–2.04 (2H,m), 2.06–2.40 (4H,m), 2.67 (3H,s), 3.74–3.96 (2H,m), 3.98–4.18 (1H,m), 4.42–4.62 (2H,m), 7.61 (1H,d), 7.85 (1H,t), 7.98 (1H,d), 9.87 (1H,d)

(12) 5-Chloro-1-propyl-1,4-dihydro-4-oxocinnoline-3-carboxylic acid (endo-8-methyl-8-azabicyclo [3.2.1]oct-3-yl) ester hydrochloride (Compound No. 39 in Table 1)

M.p. =256°–260° C. $^1$H-NMR (DMSO-$d_6$, δ ppm) 0.93 (3H,t), 1.76–1.94 (2H,m), 1.94–2.10 (2H,m), 2.10–2.32 (3H, m), 2.32–2.44 (2H,m), 2.56–2.60 (1H,m), 2.67 (3H,s), 3.72–3.92 (2H,m), 4.36–4.50 (2H,m), 5.06–5.22 (1H,m), 7.50–7.62 (1H,m), 7.83 (1H,t), 7.94 (1H,d)

(13) 5-Fluoro-N-(endo-8-methyl-8-azabicyclo[3.2.1]oct-3-yl)-8 -methyl-1-propyl-1,4-dihydro-4-oxocinnoline-3-carboxamide hydrochloride (Compound No.95 in Table 1)

M.p.=268–273 (decomp.) $^1$H-NMR (DMSO-$d_6$, δ ppm) 0.85 (3H,t), 1.70–1.88 (2H,m), 1.92–2.14 (2H,m), 2.18–2.38 (4H,m), 2.52–2.62 (1H,m), 2.67 (3H,s), 2.75 (3H,s), 3.39–3.52 (1H,m), 3.74–3.92 (2H,m), 4.04–4.18 (1H,m), 4.50–4.70 (2H,m), 7.22–7.34 (1H,m), 7.72–7.82 (1H,m), 9.95 (1H,d)

(14) 8-Chloro-N-(endo-8-methyl-8-azabicyclo[3.2.1]oct-3-yl)-1-propyl-1,4-dihydro-4-oxocinnoline-3-carboxamide hydrochloride (Compound No. 93 in Table 1)

M.p. =271–276 (decomp.) $^1$H-NMR (DMSO-$d_6$, δ ppm) 0.94 (3H,t), 1.92–2.12 (4H,m), 2.18–2.38 (4H,m), 2.39–2.50 (1H,m), 2.66 (3H,s), 3.74–3.92 (2H,m), 4.10–4.22 (1H,m), 4.80–4.96 (2H,m), 7.61 (1H,t), 8.13 (1H,d), 8.34 (1H,d), 9.99 (1H,d)

The following experiments were conducted to evaluate the biological activity of compound (I) prepared in the above Examples.

Experiment 1

$5HT_3$ Receptor Antagonistic Effect

The antagonistic activity of the compounds of the invention to $5\text{-}HT_3$ receptor was evaluated as to the inhibitory effect on the Bezold-Jarish's reflex induced in anesthetized rats with 5-HT as follows.

Male Wister strain rats (300–400 g weight) were anesthetized by peritoneal injection of urethane (1.25 g/kg) and the heart rate was monitored from an electrocardiograph. Rats were intravenously injected with physiological saline (0.5 ml/kg) and 5-HT (8 μg/kg) solution (0.5 ml/kg) in physiological saline at five minutes interval and the change in the heart rate was recorded (A). Another group of rats were intravenously injected with a test compound and 5-HT solution in the same manner as the above at five minutes interval and the change in the heart rate was recorded (B). The percent inhibition of 5-HT-induced Bezold-Jarish's reflex was calculated as follows.

Inhibition (%) =(1-B/A) x 100

Results are summarized in Table 4. In the Table, $ID_{50}$ is a dose of a compound (I) of the invention which gives a 50% inhibition. The compound number in Table 4 correspond to those in Tables 1–3.

TABLE 4

| Compound No. | B-J Reflex Inhibition ($ID_{50}$, μg/kg i.v.) |
|---|---|
| 76 | 0.3 |
| 86 | 0.15 |
| 89 | 0.02 |
| 102 | 0.2 |

The acute toxicity test of a compound (I) was conducted using three male ddy-mice (20–30 g) per each compound. A test compound was administered orally to each mouse and animals were observed for 7 days following the administration. No death was observed in animals treated with compounds (I) of the invention. This result indicates that the compounds (I) of the present invention are less toxic.

The following formulation examples are illustrative only.

Formulation 1

(1) Tablet

The following ingredients were admixed in a conventional manner and compressed on a customary tablet machine.

| | |
|---|---|
| Compound in Example 8 | 10 mg |
| Crystalline cellulose | 21 mg |
| Corn starch | 33 mg |
| Lactose | 65 mg |
| Magnesium stearate | 1.3 mg |

(2) Soft gelatin capsule

The following ingredients were admixed in a conventional manner and filled in soft capsules.

| | |
|---|---|
| Compound in Example 8 | 10 mg |
| Olive oil | 105 mg |
| Lecithin | 6.5 mg |

(3) Injection

The following ingredients were admixed in a conventional manner and filled in an ampoule in a volume of 1ml.

| | |
|---|---|
| Compound in Example 8 | 0.7 mg |
| Sodium chloride | 3.5 mg |
| Distilled water for injection | 1.0 ml |

What is claimed is:

1. A method for preventing or treating a gastroenteric disorder in a patient, which comprises administering to the patient a therapeutically effective amount of a cinnoline compound of the following formula (I):

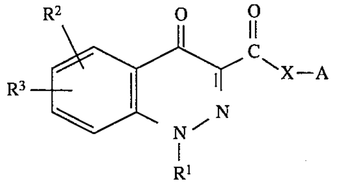

(I)

wherein X is —O— or a group of the formula:

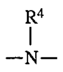

(wherein $R^4$ is a hydrogen atom or $C_1$–$C_5$ alkyl group); A is a group of the formula:

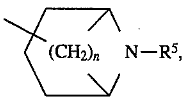

(II)

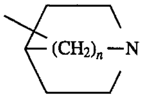

(III)

or

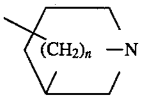

(IV)

(wherein n is an integer selected from 1 to 3; $R^5$ is a hydrogen atom, $C_1$–$C_5$ alkyl group, $C_3$–$C_8$ cycloalkyl group or $C_7$–$C_{15}$ aralkyl group); $R^1$ is a hydrogen atom, $C_1$–$C_5$ alkyl group, $C_2$–$C_5$ alkenyl group, $C_2$–$C_4$ alkynyl group, $C_3$–$C_8$ cycloalkyl group, $C_4$–$C_9$ cycloalkylalkyl group, $C_2$–$C_{10}$ alkoxyalkyl group or $C_7$–$C_{15}$ aralkyl group; $R^2$ and $R^3$ each is independently a hydrogen atom, halogen atom, trifluoromethyl group, hydroxyl group, $C_1$–$C_5$ alkoxy group, cyano group, nitro group, amino group, $C_1$–$C_5$ alkylamino group, $C_2$–$C_{10}$ dialkylamino group, $C_1$–$C_5$ alkylthio group, $C_1$–$C_5$ alkyl group, $C_3$–$C_8$ cycloalkyl group, $C_7$–$C_{15}$ aralkyl group or $C_2$–$C_{10}$ acyl group or its pharmaceutically acceptable salts, its N-oxide derivatives, or solvates thereof.

2. A method for preventing or treating nausea and/or emesis in a patient, which comprises administering to the patient a therapeutically effective amount of a cinnoline compound of the following formula (I):

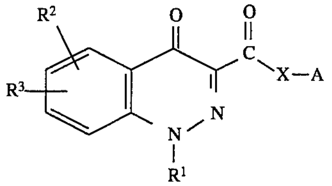

(I)

wherein X is —O— or a group of the formula:

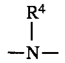

(wherein $R^4$ is a hydrogen atom or $C_1$–$C_5$ alkyl group); A is a group of the formula:

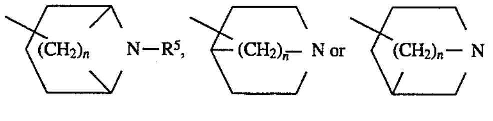

(II) (III) (IV)

(wherein n is an integer selected from 1 to 3; $R^5$ is a hydrogen atom, $C_1$–$C_5$ alkyl group, $C_3$–$C_8$ cycloalkyl group or $C_7$–$C_{15}$ aralkyl group); $R^1$ is a hydrogen atom, $C_1$–$C_5$ alkyl group, $C_2$–$C_5$ alkenyl group, $C_2$–$C_4$ alkynyl group, $C_3$–$C_8$ cycloalkyl group, $C_4$–$C_9$ cycloalkylalkyl group, $C_2$–$C_{10}$ alkoxyalkyl group or $C_7$–$C_{15}$ aralkyl group; $R^2$ and $R^3$ each is independently a hydrogen atom, halogen atom, trifluoromethyl group, hydroxyl group, $C_1$–$C_5$ alkoxy group, cyano group, nitro group, amino group, $C_1$–$C_5$ alkylamino group, $C_2$–$C_{10}$ dialkylamino group, $C_1$–$C_5$ alkylthio group, $C_1$–$C_5$ alkyl group, $C_3$–$C_8$ cycloalkyl group, $C_7$–$C_{15}$ aralkyl group or $C_2$–$C_{10}$ acyl group or its pharmaceutically acceptable salts, its N-oxide derivatives, or solvates thereof.

* * * * *